US006962930B1

(12) United States Patent
Tabakoff et al.

(10) Patent No.: US 6,962,930 B1
(45) Date of Patent: Nov. 8, 2005

(54) COMPOUNDS, COMPOSITIONS AND METHOD SUITABLE FOR AMELIORATION OF WITHDRAWAL SYNDROMES AND WITHDRAWAL-INDUCED BRAIN DAMAGE

(75) Inventors: Boris Tabakoff, Elizabeth, IL (US); Lawrence Snell, Aurora, CO (US); Paula L. Hoffman, Denver, CO (US)

(73) Assignee: Lohocla Research Corporation, Denver, CO (US)

( * ) Notice: Subject to any disclaimer, the term of this patent is extended or adjusted under 35 U.S.C. 154(b) by 1185 days.

(21) Appl. No.: 09/171,697

(22) PCT Filed: Jun. 5, 1998

(86) PCT No.: PCT/US98/11312

§ 371 (c)(1),
(2), (4) Date: Oct. 23, 1998

(87) PCT Pub. No.: WO98/55125

PCT Pub. Date: Dec. 10, 1998

Related U.S. Application Data

(60) Provisional application No. 60/048,848, filed on Jun. 6, 1997.

(51) Int. Cl.$^7$ ................ A61K 31/4706; C07D 215/42; A61P 25/08; A61P 25/22
(52) U.S. Cl. ..................................... 514/313; 546/162
(58) Field of Search .................... 546/162; 514/313

(56) References Cited

U.S. PATENT DOCUMENTS

| | | | |
|---|---|---|---|
| 5,026,700 A | 6/1991 | Harrison et al. | 514/233.8 |
| 5,135,956 A | 8/1992 | Borg et al. | 514/724 |
| 5,183,807 A | 2/1993 | della Valle et al. | 514/25 |
| 5,252,584 A | 10/1993 | Carling et al. | 514/312 |
| 5,270,309 A | 12/1993 | Leeson | 514/235.2 |
| 5,321,012 A | 6/1994 | Mayer et al. | 514/25 |
| 5,348,962 A | 9/1994 | Kulagowski et al. | 514/312 |
| 5,493,027 A | 2/1996 | Nichols et al. | 546/156 |
| 5,606,063 A | 2/1997 | Harrison et al. | 546/159 |
| 5,783,700 A * | 7/1998 | Nichols | 546/162 |
| 5,914,403 A * | 6/1999 | Nichols | 546/162 |

OTHER PUBLICATIONS

Leeson et al. J. Med. Chem. 1994, 37(24):4053-4067.*
Carling et al. J. Med. Chem. 1993, 36:3397-3408.*
Ahern, K. von B., et al, "Enhancement of NMDA Toxicity and Calcium Responses by Chronic Exposure of Cultured Cortical Neurons to Ethanol," *Neuroscience Letters, 165*, 211-214 (1994).
Brandao, F., et al., "Piracetam Impedes Hippocampal Neuronal Loss During Withdrawal After Chronic Alcohol Intake," *Alcohol, 12*(3), 279-288 (1995).
Chandler, L., et al., "Chronic Ethanol Exposure Potentiates NMDA Excitotoxicity in Cerebral Cortical Neurons", *Journal of Neurochemistry, 60*(4), 1578-1581 (1993).
Grant, K., et al., "Ethanol Withdrawal Seizures and the NMDA Receptor Complex," *European Journal of Pharmacology, 176*, 289-296 (1990).
Hoffman, P., et al. "Glutamate Receptors in Alcohol Withdrawal-Induced Neurotoxicity", *Metabolic Brain Disease, (10),1*, 73-79 (1995).
Iorio, K., et al., "Glutamate-Induced Neurotoxicity is Increased in Cerebellar Granule Cells Exposed Chronically to Ethanol" *European Journal of Pharmacology-Environmental Toxicology and Pharmacology Section, 248*, 209-212 (1993).
Iorio, K., et al., Chronic Exposure to Cerebellar Granule Cells to Ethanol Results in Increased N-Methyl-D-Aspartate Receptor Function, *Molecular Pharmacology, 41*, 1142-1148 (1992).
Khanna, J. M., et al., "Effect of NMDA Antagonists on Rapid and Chronic Tolerance to Ethanol: Importance of Intoxicated Practice," *Pharmacology Biochemistry and Behavior, 48*(3), 755-763 (1994).
Lenzi M.D. G. L., et al., "Early Treatment of Stroke with Monosialoganglioside GM-1 Efficacy and Safety Results of the Early Stroke Trial", *Stroke, 25*(8), 1552-1558 (1994).
Manev, H., et al., "Glutamate-Induced Neuronal Death in Primary Cultures of Cerebellar Granule Cells: Protection by Synthetic Derivatives of Endogenous Sphingolipids", *The Journal of Pharmacology and Experimental Therapeutics, 252*(1), 419-427 (1990).
Manev, H., et al., "Abusive Stimulation of Excitatory Amino Acid Receptors: A Strategy to Limit Neurotoxicity" , *The FASEB Journal, 4*, 2789-2797 (Jul., 1990).

(Continued)

*Primary Examiner*—Evelyn Mei Huang
(74) *Attorney, Agent, or Firm*—Olson & Hierl, Ltd.

(57) ABSTRACT

Compounds, composition and method for ameliorating alcohol or drug dependency withdrawal syndromes and withdrawal-induced brain damage are disclosed. In particular, a series of N-substituted-4-uredo-5,7-dihalo-2-carboxy quinoline compounds are disclosed having combined properties as antagonists of voltage-sensitive sodium channels (VSNaC) and as selective competitive antagonists at the strychnine-intensive glycine site of N-methyl-D-aspartate (NMDA) receptors. The disclosed compounds prevent or reduce the signs and symptoms of neurohyperexcitability and particularly the neurohyperexcitability associated with withdrawal syndrome manifested by patients upon withdrawal from chronic use of dependence inducing agents (e.g. ethanol, barbiturates, opiates etc.). The combined actions of the disclosed compound on VSNaC and NMDA receptors also impart properties to these compounds that are important in preventing and reducing excitotoxic neurodegeneration and reducing anxiety without the undesirable CNS depressant side-effects of agents hitherto employed for these purposes.

12 Claims, 14 Drawing Sheets

OTHER PUBLICATIONS

Rabbani, M., et al., "Possible Involvement of NMDA Receptor-Mediated Transmission in Barbiturate Physical Dependence", *British Journal of Pharmacology, 111*, 89-96, (1994).

Schneider, PhD, J., et al. "GM1 Ganglioside Treatment of Parkinson's Disease: An Open Pilot Study of Safety and Efficacy", *Neurology, 45*, 1149-1154, (Jun., 1995).

Jaffee, J., "Drug Addiction and Drug Abuse", Ch. 22 in *Goodman and Gilman's The Pharmacological Basis of Therapeutics*, (Gilman A.G., et al. eds.), 522-573, Pergamon Press, New York (8th Ed. 1990).

Rall, T., et al., "Hypnotics and sedatives: Ethanol," Ch. 17 in *Goodman and Gilman's The Pharmacological Basis of Therapeutics*, (Goodman, A.G., et al., eds), 436-462, Pergamon Press, New York, (8th ed., 1990).

Ripley, T.L., et al., "Effects on Ethanol Withdrawal Hyperexcitability of Chronic Treatment with a Competitive N-Methyl-D-Aspartate Receptor Antagonist," *The Journal of Pharmacological and Experimental Therapeutics, 272(1)*, 112-118 (1995).

Szabó, G., et al. "The NMDA Receptor Antagonist Dizocilpine Differentially Affects Environment-Dependent and Environment-Independent Ethanol Tolerance," *Psychopharmacology, 113*, 511-517 (1994).

Tabakoff, Boris., et al., "Biology of Tolerance and Dependence", *Medical and Social Aspects of Alcohol Abuse*, (Tabakoff et al. eds.), 187-220, Plenum Press, New York, (1983).

Wallis, C., et al., "GM1 Ganglioside Reduces Ethanol Intoxication and the Development of Ethanol Dependence," *Alcohol, 12(6)*, 573-580, (1995).

* cited by examiner

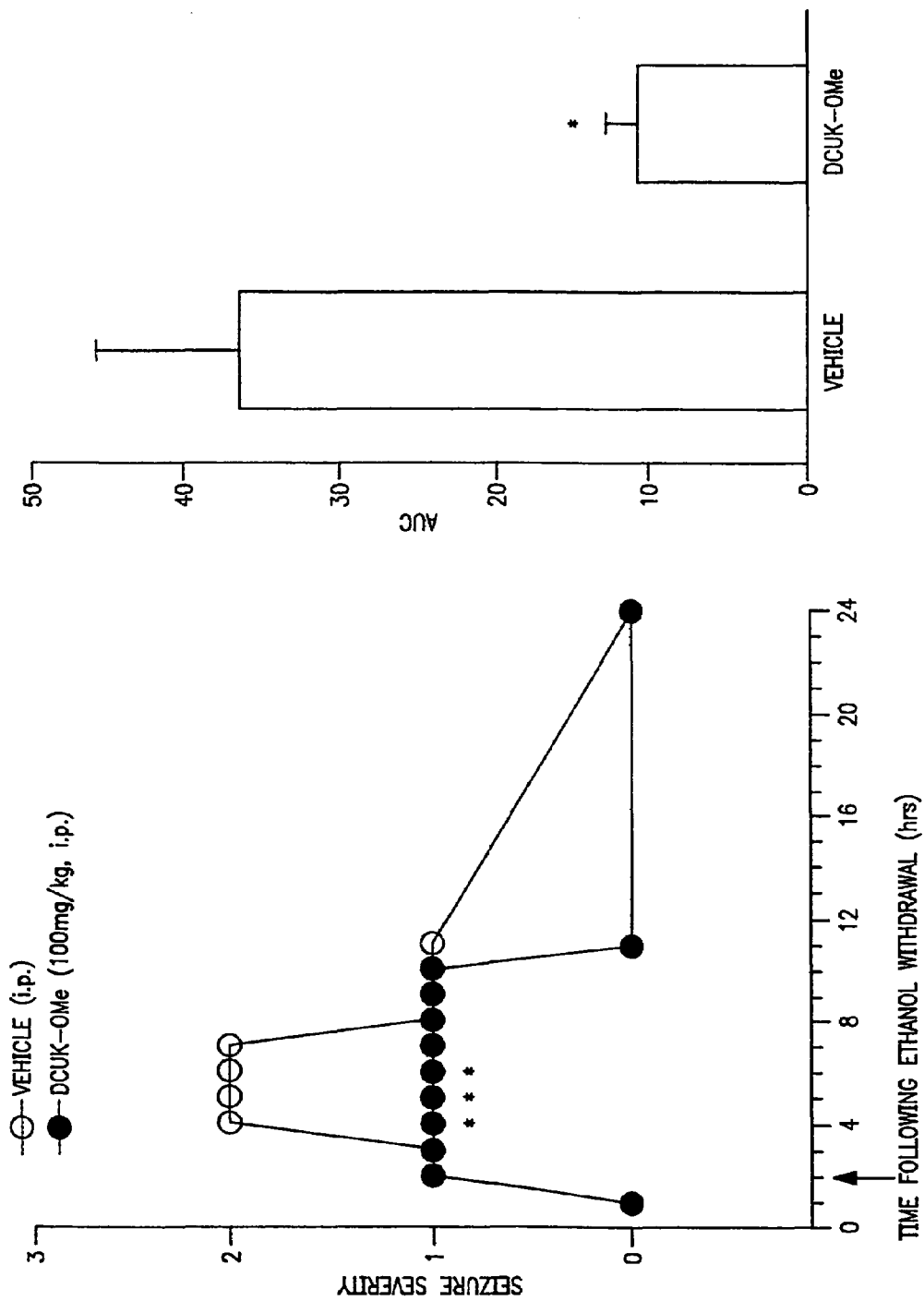

COMPOUNDS, COMPOSITIONS AND METHOD SUITABLE FOR AMELIORATION OF WITHDRAWAL SYNDROMES AND WITHDRAWAL-INDUCED BRAIN DAMAGE

CROSS-REFERENCED TO RELATED APPLICATION

This application is a 371 of PCT/US98/11312, filed on Jun. 5, 1998, and claims the benefit of the filing date of U.S. Provisional Application Ser. No. 60/048,848, filed on Jun. 6, 1997.

FIELD OF THE INVENTION

This invention relates to compounds, compositions and methods suitable for ameliorating withdrawal syndromes. More particularly, this invention relates to amelioration of alcohol withdrawal, drug withdrawal and withdrawal-induced brain damage.

BACKGROUND OF THE INVENTION

Pharmacological science has maintained that there exists a structure-activity relationship in which the chemical structure of a compound of interest (drug) determines the pharmacological selectivity and potency of the drug See, for example, Ross E., chapter on "PHARMACODYNAMICS: MECHANISMS OF DRUG ACTION AND THE RELATIONSHIP BETWEEN DRUG CONCENTRATION AND EFFECT," in Hardman J. D., et al., eds., *Goodman and Gilman's The Pharmacological Basis of Therapeutics*, 9th edition, pp. 29–41, McGraw-Hill, New York (1990), (hereinafter "*Goodman and Gilman's* 9th Edition"). In many instances, structural entities (pharmacophores) have been identified within the overall chemical structure of a drug, which are critical for the drug's specificity of action.

For example, when one examines the structure of several anticonvulsant agents such as diphenylhydantoin, phenobarbital, and carbamazepine, which have all been shown to inhibit the action of voltage-sensitive sodium channels in a use-dependent manner, (McNamara J. O., chapter on "DRUGS EFFECTIVE IN THE THERAPY OF THE EPILEPSIES," in *Goodman and Gilman's*, 9th edition), one notes that these compounds all contain a diphenylureido group (or a group that can resemble a diphenylureido group in three dimensional space) as part of their overall structure. The structural characteristics of compounds acting at the strychnine insensitive glycine site of the N-methyl-D-aspartate (NMDA) subtype of the glutamate receptor have also been examined and kynurenic acid derivatives have been defined as exemplary structures which can act as glycine antagonists at this site and inhibit the function of the NMDA receptor-gated ion channels (Leeson P. D., et al., "THE GLYCINE SITE ON THE NMDA RECEPTOR: STRUCTURE-ACTIVITY RELATIONSHIPS AND THERAPEUTIC POTENTIAL," *J. Med. Chem.*, 37 4053–4067 (1994).

Both the overactivity of voltage-sensitive sodium channels and NMDA receptor-gated ion channels has been implicated in CNS hyperexcitability states that arise from a diverse etiology ranging from epilepsy (McNamara J. O., chapter on "DRUGS EFFECTIVE IN THE THERAPY OF THE EPILEPSIES," Goodman and Gilman's, 9th edition, pp. 461–486; MacDonald R. L. et al., chapter on "GENERAL PRINCIPLES: PRINCIPLES OF ANTIEPILEPTIC DRUG ACTION," in Levy R., et al., *Antiepiletic Drugs*, 3rd edition, Raven Press, New York (1989), to ethanol withdrawal. Thus, a chemical compound containing both the pharmacophore which is considered important for inhibiting voltage-sensitive sodium channels and a pharmacophore effective in inhibiting the NMDA receptor-gated ion channels, and having the duality of action particularly important for controlling central nervous system (CNS) hyperexcitability arising from ethanol withdrawal, other drug withdrawal, and other pathological conditions would be highly desirable.

Ethanol belongs to a class of pharmacologic agents that also includes other sedatives and hypnotics, such as barbiturates and benzodiazepines. The chronic and excessive ingestion or administration of ethanol (beverage alcohol), other agents with a similar pharmacologic profile (e.g., benzodiazepines and barbiturates), and analgesics (opiates) produces significant changes in CNS function in human beings and other animals. These neuroadaptive changes in CNS function in response to the depressant actions of ethanol and other similar drugs or analgesic actions of opiates result from modification of the normal chemical communication within specific pathways which mediate information flow through assemblages of brain neurons. These significant changes in CNS function, in general, result in a withdrawal syndrome which includes signs of CNS hyperexcitability when the chronic ingestion or administration of ethanol, other CNS depressant drugs, or opiates is abruptly terminated.

The withdrawal syndrome includes such manifestations of CNS hyperexcitability as tremors, insomnia, anorexia, seizures, convulsions, etc. The presence of a withdrawal syndrome related to the termination of administration of ethanol or other drug, e.g., barbiturate, or morphine is prima facie evidence that the individual is physically dependent on the drug being chronically ingested/administered. See, generally, Tabakoff, B. et al., "BIOLOGY OF TOLERANCE AND DEPENDENCE," in Tabakoff, B., et al., eds. *Medical and Social Aspects of Alcohol Abuse*, pp. 187–220, Plenum Press, New York (1983); and Jaffe, J. H., chapter on "DRUG ADDICTION AND DRUG ABUSE," in Gilman, A. G., et al., eds., *Goodman and Gilman's The Pharmacological Basis of Therapeutics*, 8th edition, pp. 522–573, Pergamon Press, New York (1990) (hereinafter "Goodman and Gilman's, 8th Edition"). Also, Edwards, G. "THE ALCOHOL DEPENDENCE SYNDROME: A CONCEPT AS STIMULUS TO ENQUIRY," British Journal of Addiction, 81 171–183, 1986; Wikler, G., "DYNAMICS OF DRUG DEPENDENCE: IMPLICATIONS OF A CONDITIONING THEORY FOR RESEARCH AND TREATMENT," *Arch. Gen. Psychiatry*, 28 611–616 (1973) and others have written extensively that avoidance of signs and symptoms of ethanol and other drug withdrawal are the impetus for further drug-taking behavior, and relapse occurs, in part, as an attempt at self-medicating withdrawal signs. One can thus contemplate that an efficacious medication for treatment of addictive drug withdrawal would also be efficacious in promoting the termination of drug-taking behavior and preventing relapse in those individuals who stop ingesting alcohol or other drugs. There is currently no single class of compounds suitable for the treatment of drug withdrawal syndromes because the current therapies are with medications which have cross-dependence potential (e.g., benzodiazepines and methadone) or treat only a limited portion of the withdrawal syndrome (e.g., propranolol for ethanol withdrawal).

Current therapies include: (a) transfer to less efficacious compounds (e.g., methadone) for opiate withdrawal; (b) treatment with sympatholytics (e.g., the β-adrenergic receptor antagonist propranolol or the $\alpha_2$-adrenergic receptor agonist clonidine) for opiate or ethanol withdrawal; and (c) treatment with anxiolytics, neuroleptics or sedatives (e.g., benzodiazepines or barbiturates) for ethanol withdrawal.

Research has demonstrated that the signs and symptoms of ethanol, barbiturate, and opiate withdrawal syndromes are quite similar in humans and lower animal species. Because of this similarity, the underlying neurochemical mechanisms of the human manifestations of ethanol, barbiturate, and opiate physical dependence and drug withdrawal can be predictively studied in non-human mammalian animal species.

Studies have demonstrated that the chronic treatment of mice with ethanol or barbiturates results in the up-regulation of the function of the brain excitatory neurotransmitter systems (i.e., the neuronal systems which use glutamate as a neurotransmitter substance). See, for example, Grant, K. A., et al., "ETHANOL WITHDRAWAL SEIZURES AND THE NMDA RECEPTOR COMPLEX," Eur. J. Pharmacol, 176 289–296 (1990); Rabbani, M. et al., "POSSIBLE INVOLVEMENT OF NMDA RECEPTOR-MEDIATED TRANSMISSION IN BARBITURATE PHYSICAL DEPENDENCE," Brit. J. Pharmacol., 111 89–96, (1994). In particular, chronic exposure to ethanol or barbiturates results in an increased number of the receptors for glutamate known as the N-methyl-D-aspartate (NMDA) receptors. Similarly, the development of tolerance to and physical dependence on opiates has been shown to involve NMDA receptors. See, Elliott, K., et al., "N-METHYL-D-ASPARTATE(NMDA) RECEPTORS, MU AND KAPPA OPIOID TOLERANCE, AND PERSPECTIVES ON NEW ANALGESIC DRUG DEVELOPMENT," Neuropsychopharmacol., 13 347–356 (1995).

The increase in NMDA receptor function has been linked at the molecular and cellular level with the generation of the characteristic signs of CNS hyperexcitability during withdrawal from drugs such as ethanol, barbiturates, or opiates. A number of compounds which are inhibitors of NMDA receptor function have been proposed and tested as treatments for the ethanol withdrawal syndrome. However, such medications, particularly agents acting as blockers of the NMDA receptor ion channel and those competing with glutamate at the glutamate binding site, have a significant drawback, since such NMDA receptor antagonists themselves interfere with cognitive function. See Collingridge, G. L., et al., "EXCITATORY AMINO ACID RECEPTORS IN THE VERTEBRATE CENTRAL NERVOUS SYSTEM," Pharmacol, Rev., 40 143–210 (1989). Recent work has also suggested that the non-competitive NMDA receptor antagonist, dizocilpine maleate (MK-801), reduces the development of morphine tolerance as well as the effects of withdrawal (Trujillo, K. A. et al., "EXCITATORY AMINO ACIDS AND DRUGS OF ABUSE: A ROLE FOR N-METHYL-D-ASPARTATE RECEPTORS IN DRUG TOLERANCE, SENSITIZATION AND PHYSICAL DEPENDENCE," Drug Alcohol Depend., 38 139–154 (1995)), but only at doses which are known to induce marked behavioral stimulation and ataxia.

The NMDA receptor glycine site antagonists have been introduced to overcome some of the negative effects of the other NMDA receptor antagonists. See Lesson, P. D., et al., "THE GLYCINE SITE ON THE NMDA RECEPTOR: STRUCTURE-ACTIVITY RELATIONSHIPS AND THERAPEUTIC POTENTIAL," J. Med. Chem., 37 4053–4067 (1994). Such agents do possess some anticonvulsant activity (Rowley, M., et al., "3-ACYL-4 HYDROXYQUINOLINE-2(1H)-ONES. SYSTEMICALLY ACTIVE ANTICONVULSANTS ACTING BY ANTAGONISM AT THE GLYCINE SITE OF THE N-METHYL-D-ASPARTATE RECEPTOR COMPLEX, " J. Med. Chem., 36 3386–3396 (1993)), but the prototypical members of this class of agents, the R-(+) isomer of 3-amino-1-hydroxypyrrolidin-2-one, (±)HA-966, and 7-chlorokynurenate, have demonstrated a relative ineffectiveness at reducing or preventing the signs and symptoms of opiate withdrawal (Kosten, T. A., et al., "THE SEVERITY OF NALOXONE-PRECIPITATED OPIATE WITHDRAWAL IS ATTENUATED BY FELBAMATE, A POSSIBLE GLYCINE ANTAGONIST," Neuropsychopharmacology, 13 323–333 (1995)) and ethanol withdrawal.

In generalized neuroexcitability disorders, that include drug withdrawal and some forms of epilepsy, two distinct phenomena important to the generation of seizures can be distinguished, i.e., initiation (development of seizure focus) and propagation (spread of seizure to contiguous and distant anatomical sites. See Rall, T. W., et al., chapter on "DRUGS EFFECTIVE IN THE THERAPY OF THE EPILEPSIES" in Goodman and Gilman's, 8th edition, pp. 436–462. Blockade of generalized seizure initiation is amenable to therapeutic strategies employing NMDA receptor antagonists (Croucher, M. J., et al., "7-CHLOROKYNURENIC ACID, A STRYCHNINE-INSENSITIVE GLYCINE RECEPTOR ANTAGONIST, INHIBITS LIMBIC SEIZURE KINDLING," Neurosci. Lett., 118 29–32 (1990)). Agents which block propagation of neuroexcitability by blocking, in a use-dependent manner, voltage-sensitive sodium channels, have been used to block propagation and control epilepsy-related generalized seizures. These compounds have low levels of sedation, but the aura associated with initiation events is not controlled by such agents.

Carbamazepine is prototypic of the general class of voltage-sensitive sodium channel blockers and although it has been employed to treat ethanol withdrawal in humans, its effectiveness is equivocal (Erstad, B. L., et al., "MANAGEMENT OF ETHANOL WITHDRAWAL," Am. J. Health-Syst. Pharm., 52 697–709 (1995)). Animal studies show that carbamazepine is not effective in reducing, by itself, the signs and symptoms of ethanol withdrawal (Grant K. et al., "COMPARISON OF THE EFFECTS OF THE UNCOMPETITIVEN-METHYL-D-ASPARTATE ANTAGONIST (±)-5-AMINOCARBONYL-10, 11-DIHYDRO-5H-DIBENZO [A,D]CYCLOHEPTEN-5,10-IMINE (ADCI) WITH ITS STRUCTURAL ANALOGS DIZOCILPINE (MK-801) AND CARBAMAZEPINE ON ETHANOL WITHDRAWAL SEIZURES," J. Pharmacol. Exp. Ther., 260 1017–1022 (1992)).

Physical dependence on ethanol and other sedatives or hypnotics can generate deleterious effects on the CNS in addition to generating signs of withdrawal. A significant portion of the brain damage evident in alcoholics is likely to be the cumulative result of multiple withdrawal episodes during the lifetime of these individuals. The deleterious effect of ethanol withdrawal on brain morphology has been demonstrated. See, for example, Brandao, F., et al., "PIRACETAM IMPEDES HIPPOCAMPAL NEURONAL LOSS DURING WITHDRAWAL AFTER CHRONIC ETHANOL INTAKE," Alcohol, 12 279–288 (1995); and Daryanani, H. E., et al., "ALCOHOLIC WITHDRAWAL SYNDROME AND SEIZURES," Alcohol & Alcoholism, 29 323–328 (1994).

The deleterious effects of ethanol dependence and withdrawal have also been demonstrated in in vitro studies in which neurons exposed chronically to ethanol in culture are more susceptible to excitotoxic effects of glutamate, following ethanol withdrawal. See, for example, Iorio, K. R., et al., "GLUTAMATE-INDUCED NEUROTOXICITY IS INCREASED IN CEREBELLAR GRANULE CELLS EXPOSED CHRONICALLY TO ETHANOL," *Eur. J. Pharmacol.,* 248 209–212 (1993); Ahern, K. B., et al., "ENHANCEMENT OF NMDA TOXICITY AND CALCIUM RESPONSES BY CHRONIC EXPOSURE OF CULTURED CORTICAL NEURONS TO ETHANOL," *Neurosci. Lett.,* 165 211–214 (1994); and Chandler, L. J., et al., "CHRONIC ETHANOL EXPOSURE POTENTIATES NMDA EXCITOTOXICITY IN CEREBRAL CORTICAL NEURONS," *J. Neurochem.,* 60 1578–1581 (1993).

The increased excitotoxicity in the ethanol-withdrawn cells has also been explained by the up-regulation of the number of NMDA receptors caused by chronic exposure of the neurons to ethanol. Thus, there is a need for medications to treat dependence on or prevent the withdrawal syndrome from ethanol (or barbiturate) usage that beneficially ameliorate ethanol withdrawal-induced neuronal damage.

Since the pharmacological specificity of a chemical compound is determined by structural entities (pharmacophores) which are part of the overall structure of the pharmacologically active agent, an ideal compound would combine two or more pharmacophores with specific pharmacological properties to embody the pharmacological properties of both pharmacophores. In particular, a compound designed to possess, in one molecule, properties to both block voltage-sensitive sodium channels and to antagonize the glycine site of the NMDA receptor would be of far greater utility in controlling drug withdrawal CNS hyperexcitability than agents currently available. This invention provides a series of novel compounds that embody such pharmacological properties.

SUMMARY OF THE INVENTION

Compounds, compositions and a method suitable for treating withdrawal syndromes, particularly arising from alcohol or drug dependence and withdrawal or withdrawal-induced brain damage manifested in a patient suffering withdrawal symptoms is disclosed. The term "withdrawal syndromes" as used herein includes, but is not limited to, manifestations of one or more symptoms of CNS hyperexcitability associated with alcohol withdrawal syndromes, neuroexcitability disorders associated with drug withdrawal syndromes, neural brain damage induced by alcohol or drug dependence withdrawal and like neurodegenerative disorders associated with chronic drug use and withdrawal.

A preferred method comprises administering a physiologically effective amount of a compound having the general formula (I):

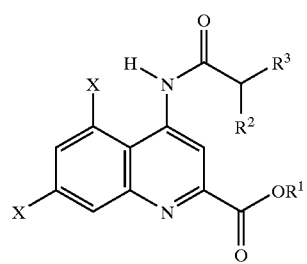

(I)

a tautomer thereof, a pharmacologically acceptable ester, amide, salt, ether, or an acid addition salt thereof;

wherein $R^1$ represents hydrogen or an alkyl group of 1 to 6 carbon atoms;

$R^2$ and $R^3$ each independently represent phenyl which may be unsubstituted or substituted one or more times with substituents selected from the group consisting of alkoxy, cycloalkoxy, alkyl, and cycloalkyl groups containing up to 6 carbon atoms, hydrogen, hydrocarbon selected from the group consisting of straight chain, branched, cyclic, and heterocyclic groups containing up to 18 carbon atoms, halogen, cyano, trifluoromethyl, nitro, —$OR^a$, —$SR^a$, —$NR^aR_b$, $NR^aCOR^b$, —$NR^aCO_2R^b$, —$NR^aSO_2R^b$, —$NR^iCZNR^aR^b$, —$CO_2$, or —$CONR^aR^b$; wherein $R^a$, $R^b$, $R^i$ each independently represent hydrogen or hydrocarbon as described above and can be the same or different and Z represents oxygen, sulphur, or a group of formula =N,E; wherein E represents hydrocarbon as described above or an electron-withdrawing group; or $R^2$ and $R^3$ together with the intervening carbon atom represent carbonyl (C=O), thiocarbonyl (C=S), imino (C=N,$R^a$), oximino (C=N,$OR^a$), or a 3- to 8-membered ring containing from zero to 4 hetero-atoms selected from the group consisting of oxygen, nitrogen, sulphur and phosphorus; wherein $R^a$ represents hydrogen or hydrocarbon as described above;

wherein each of the $R^2$ and $R^3$ substituents can be the same or different; and X represents halogen and each of the 5, 7, substituents can be the same or different.

Administration of the compound can be by oral, intravenous, subcutaneous, intramuscular, intraperitoneal, transdermal or buccal means for therapeutic treatment.

Preferred compounds of the general formula (1) are N-substituted 4-ureido-5,7-dihalo-2-carboxy quinoline compounds. Particularly preferred compounds were derivatives of kynurenic acid, hereafter referred to generally as DCUK compounds. Presently preferred DCUK compounds are (N,N-diphenyl)-4-ureido-5,7-dichloro-2-carboxy-quinoline(DCUKA); (N,N-diphenyl)-4-ureido-5,7-dichloro-2-carboxy-quinoline methyl ester)(DCUK-OMe); and N-phenyl, N-[2-methoxy]phenyl)-4-ureido-5,7-dichloro-2-carboxy-quinoline(MeO-DCUKA) which demonstrate affinity for both the strychnine-insensitive glycine binding site on the NMDA receptor complex and voltage-sensitive sodium channels.

The inventive DCUK compounds beneficially possess activity in reducing drug withdrawal-induced and excitotoxin-induced CNS hyperexcitability and neuronal damage at doses devoid of CNS depressant effects. Even at high doses, the DCUK compounds efficiently inhibit, in a use dependent manner, voltage sensitive sodium channels and inhibit NMDA receptor function without inducing the adverse marked behavioral stimulation and ataxia effects associated with known NMDA receptor antagonists or voltage sensitive sodium channel blockers. Additionally, the inventive DCUK compounds beneficially reduce or prevent in vitro measures of glutamate excitotoxicity.

BRIEF DESCRIPTION OF THE DRAWINGS

In the drawings,

FIG. 6 shows the protective effects of DCUK-OMe on ethanol withdrawal-induced seizures in C57BL/6 mice;

DETAILED DESCRIPTION OF PREFERRED EMBODIMENT

Figure 1A:
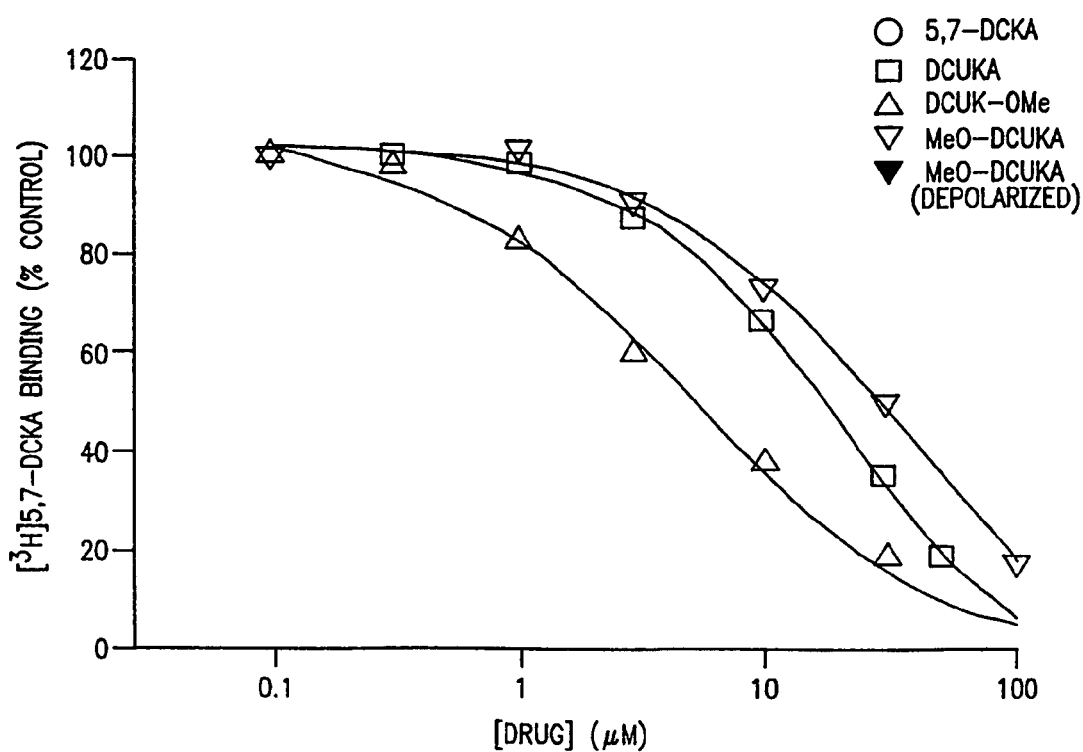
FIG. 1 shows the effects of DCUK compounds on the binding of [$^3$H]5,7-dichlorokynurenate ([3H]5,7-DCKA) to rat cortical membranes (1A) and the binding of [$^3$H]batrachotoxinin ([3H]BTX) to rat cortical synaptosomes (1B)

Disclosed are compounds, compositions and a method suitable for treating dependence on, or preventing the withdrawal syndrome from being manifested during withdrawal from, the chronic use of ethanol, or other sedative or hypnotic or analgesic drugs in a patient (humans or other mammalian animal species). Withdrawal syndrome manifestations include, but are not limited to CNS hyperexcitability, such as tremors, insomnia, anorexia, disorientation, seizures, convulsions, anxiety or the like. The present compounds, compositions and method also provide for treating neurodegenerative disorders associated with chronic drug use and withdrawal induced brain damage.

The method provided by the present invention comprises administering by systemic means to a patient in need of such treatment or prevention an effective ameliorating amount of a compound which exhibits both an affinity for the strychnine-insensitive glycine binding site on the NMDA receptor complex and affinity for voltage-sensitive sodium channels (VSNaC).

A preferred compound embodiment has the general formula (I):

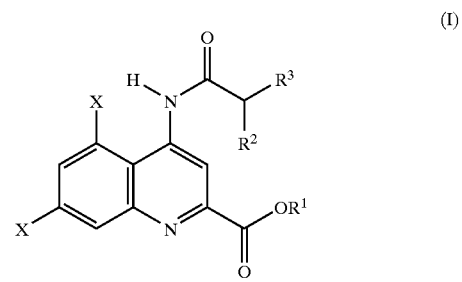

a tautomer thereof, a pharmacologically acceptable ester, amide, salt, ether, or an acid addition salt thereof;

wherein $R^1$ represents hydrogen or an alkyl group of 1 to 6 carbon atoms;

$R^2$ and $R^3$ each independently represent phenyl which may be unsubstituted or substituted one or more times with substituents selected from the group consisting of alkoxy, cycloalkoxy, alkyl, and cycloalkyl groups containing up to 6 carbon atoms, hydrogen, hydrocarbon selected from the group consisting of straight chain, branched, cyclic, and heterocyclic groups containing up to 18 carbon atoms, halogen, cyano, trifluoromethyl, nitro, —$OR^a$, —$SR^a$, —$NR^aR^b$, $NR^aCOR^b$, —$NR^aCO_2R^b$, —$NR^aSO_2R^b$, —$NR^iCZNR^aR^b$, —$CO_2$, or —$CONR^aR^b$; wherein $R^a$, $R^b$, $R^i$ each independently represent hydrogen or hydrocarbon as described above and can be the same or different and Z represents oxygen, sulphur, or a group of formula =N,E; wherein E represents hydrocarbon as described above or an electron-withdrawing group; or $R^2$ and $R^3$ together with the intervening carbon atom represent carbonyl (C=O), thiocarbonyl (C=S), imino (C=N,$R^a$), oximino (C=N,$OR^a$), or a 3- to 8-membered ring containing from zero to 4 hetero-atoms selected from the group consisting of oxygen, nitrogen, sulphur and phosphorus; wherein $R^a$ represents hydrogen or hydrocarbon as described above;

wherein each of the $R^2$ and $R^3$ substituents can be the same or different; and X represents halogen and each of the 5, 7, substituents can be the same or different.

The term "alkyl" as used herein refers to lower alkyl groups containing less than 7 carbon atoms. A preferred alkyl group has 1 to 3 carbon atoms. The term "hydrocarbon" as used herein includes straight-chained, branched, and cyclic groups, including heterocyclic groups, containing up to 18 carbon atoms, suitably up to 15 carbon atoms, and conveniently up to 12 carbon atoms. The term "halogen" as used herein includes chloro, fluoro, bromo and iodo substituents, preferably chloro. The term "alkoxy" as used herein refers to alkoxy groups containing less than 7 carbon atoms, preferably 1 to 3 carbon atoms. The term "substituted phenyl" refers to phenyl having one or more substituents selected from the group consisting of alkoxy, cycloalkoxy, alkyl, and cycloalkyl groups containing up to 6 carbon atoms. A preferred phenyl has an alkoxy group substituent having 1 to 3 carbon atoms.

For convenience, N-substituted-4-ureido-5,7-dihalo-2-carboxy quinolines of formula (1) will be referred to herein simply as the compounds of formula I. In one presently preferred compound of formula (I), each of the X substituents is chloro, $R^1$, is hydrogen, and $R^2$ and $R^3$ each is a phenyl group; in another preferred compound of formula (1), each of the X substituents is chloro, $R^1$ is an alkyl group having 1 to 3 carbon atoms, and $R^2$ and $R^3$ each is a phenyl group. In yet another preferred compound of formula (I), each of the X substituents is chloro, $R^1$, is hydrogen, one of $R^2$ and $R^3$ is an unsubstituted phenyl group and the other is phenyl having an alkoxy substituent having 1 to 3 carbon atoms. A particularly preferred compound of formula I is an N-substituted-4-ureido-5,7-dichloro-quinolinic acid.

The salts of the compounds of formula I preferably are non-toxic, pharmaceutically acceptable salts suitable for medical use. Other salts may, however, be useful in the preparation of the compounds according to the invention or in the preparation of their non-toxic pharmaceutically acceptable salts. Suitable pharmaceutically acceptable salts of the compounds of this invention include alkali metals salts, e.g., sodium or potassium salts; alkaline earth metal salts, e.g., calcium or magnesium salts; and salts formed with suitable organic ligands e.g., quaternary ammonium salts. When appropriate, acid addition salts may, for example, be formed by mixing a solution of the compound prepared according to the invention with a solution of a pharmaceutically acceptable non-toxic acid such as hydrochloric acid, fumaric acid, maleic acid, succinic acid, acetic acid, citric acid, tartaric acid, carbonic acid, or phosphoric acid.

In a preferred method embodiment, the compounds of formula I are administered via a pharmaceutical formulation. Suitable formulations of the present invention comprise at least one compound of this invention present in a therapeutically or pharmaceutically effective dose level, optionally together with one or more pharmaceutically acceptable additional ingredients, such as sympatholytics, e.g., the β-adrenergic receptor antagonist propranolol, or the $α_2$-adrenergic receptor agonist clonidine or anxiolytics such as benzodiazepines or barbiturates.

The invention also provides a method suitable for treating or preventing convulsions arising from conditions other than drug withdrawal, such as epilepsy, febrile seizures, poisoning by exogenous and endogenous excitatory neuroreceptor agonists, or inhibitory neuroreceptor antagonists and neurotoxins, including environmental neurotoxins. The method comprises administering to a patient in need of such treatment or prevention an effective amount of an antagonist compound exhibiting affinity for both the strychnine-insensitive glycine binding site on the NMDA receptor complex and affinity for voltage dependent sodium channels.

In addition, the present invention also provides a method suitable for treating or preventing neurodegenerative disorders arising from conditions, other than drug withdrawal, such as but not limited to stroke, hypoglycemia, cerebral palsy, transient cerebral ischemic attack, perinatal asphyxia, epilepsy, Huntington's chorea, Alzheimer's disease, Amyotrophic Lateral Sclerosis, Parkinson's disease, olivo-pontocerebellar atrophy, anoxia such as from drowning, spinal cord and head injury, and poisoning by exogenous and endogenous excitatory neuroreceptor agonists, or inhibitory neuroreceptor antagonists and neurotoxins, including environmental neurotoxins, comprising administering to a patient in need of such treatment or prevention an effective amount of an antagonist compound exhibiting affinity for both the strychnine-insensitive glycine binding site on the NMDA receptor complex and for voltage dependent sodium channels. Preferably the compound freely crosses the blood brain barrier. Preferably the compound of formula I is an N-substituted-4-ureido-5,7-dihalo-quinolinic acid, a tautomer, or pharmacologically acceptable ester, amide, salt, ether, and acid addition salt thereof.

The present invention is also useful as a method suitable for treating or preventing anxiety arising from conditions other than drug withdrawal, such as, but not limited to, panic disorder, phobias, obsessive-compulsive disorder, and personality disorder, comprising administering by systemic means to a patient in need of such treatment or prevention an effective amount of an antagonist compound exhibiting affinity for both the strychnine-insensitive glycine binding site on the NMDA receptor complex and for voltage dependent sodium channels. Preferably the compound freely crosses the blood brain barrier. A preferred compound embodiment is an N-substituted 4-ureido-5,7-dihalo- quinolinic acid of the formula I, a tautomer, or pharmacologically acceptable ester, amide, salt, ether, and acid addition salt thereof. More preferably, the compound of formula I is an N-substituted 4-ureido-5,7-dichloro-quinolinic acid.

Alternatively, the present invention may be suitably used as a method of treating or preventing schizophrenia, comprising administering by systemic means to a patient in need of such treatment or prevention an effective amount of an antagonist compound exhibiting affinity for both the strychnine-insensitive glycine binding site on the NMDA receptor complex and for voltage dependent sodium channels. Preferably the compound freely crosses the blood brain barrier. Preferably the compound of formula I is an N-substituted-4-ureido-5,7-dihalo-quinolinic acid, a tautomer, or pharmacologically acceptable ester, amide, salt, ether, and acid addition salt thereof.

The method and compositions of the present invention may also be suitable for use for reducing or preventing the development of tolerance to opiates or other beneficial drugs. The method comprises administering by systemic means to a patient in need of such treatment or prevention an effective amount of an antagonist compound of formula I exhibiting affinity for both the strychnine-insensitive glycine binding site on the NMDA receptor complex and for voltage dependent sodium channels. Preferably the compound freely crosses the blood brain barrier. More preferably the compound of formula I is an N-substituted-4-ureido-5,7-dihalo-quinolinic acid, a tautomer, or pharmacologically acceptable ester, amide, salt, ether, and acid addition salt thereof.

In a preferred method embodiment, the compounds of formula I may be administered concomitantly with or prior to administration of a tolerance-producing but otherwise beneficial compound. In a composition embodiment, a composition may contain a tolerance producing compound and an effective amount of an antagonist compound of formula I exhibiting affinity for both the strychnine-insensitive glycine binding site on the NMDA receptor complex and for voltage dependent sodium channels as a combined preparation for simultaneous, separate or sequential use in the therapy of a disorder in which treatment with the tolerance-inducing compound is beneficial.

The disclosed compounds can be administered as part of a pharmaceutical composition comprising a pharmaceutically acceptable carrier. Pharmaceutically acceptable carriers include water, saline, buffers, and other compounds described, e.g., in The Merck Index, Merck & Co., Rahway, N.J. and like references familiar to those skilled in the pharmaceutical arts. The inventive pharmaceutical composition can be administered by oral, intravenous, subcutaneous, intramuscular, intraperitoneal, transdermal or buccal means for therapeutic treatment. The pharmaceutical composition can be administered in a variety of unit dosage forms depending upon the method of administration. For example, unit dosage forms suitable for oral administration include powder, tablets, pills, capsules, solutions, suspensions, emulsions, capsulets, dragees and the like.

Compositions for intravenous administration preferably comprise a solution of the compound dissolved or suspended in an acceptable carrier, preferably an aqueous carrier.

For solid dosage form compositions, conventional substantially non-toxic solid carriers can be used. Suitable carriers include, without limitation thereto, pharmaceutical grades of mannitol, lactose, starch, magnesium stearate, sodium saccharin, talcum, cellulose, glucose, sucrose, magnesium carbonate, and the like. For oral administration, a composition comprises at least one pharmaceutically acceptable excipient, such as those carriers previously listed, and about 0.1 weight percent to about 95 weight percent of the compound of formula I as active ingredient. Preferably the composition comprises about 20 weight percent active ingredient.

Compounds can be administered as a single daily dose or preferably divided doses on a daily basis, which will vary with the nature of the active ingredient. Doses of up to about 500 mg/kg of body weight may be administered. Preferably for a human patient, a dose in the range of about 10 to about 100 mg/kg of body weight may be administered from one to about 3 times per day or as necessary to prevent or ameliorate withdrawal symptoms.

One preferred compound embodiment, (N,N-diphenyl)-4-ureido-5,7-dichloro-2-carboxy-quinoline(DCUKA), was synthesized as a derivative of kynurenic acid in the synthesis phases I–V as explained and illustrated below, but is not limited thereto.

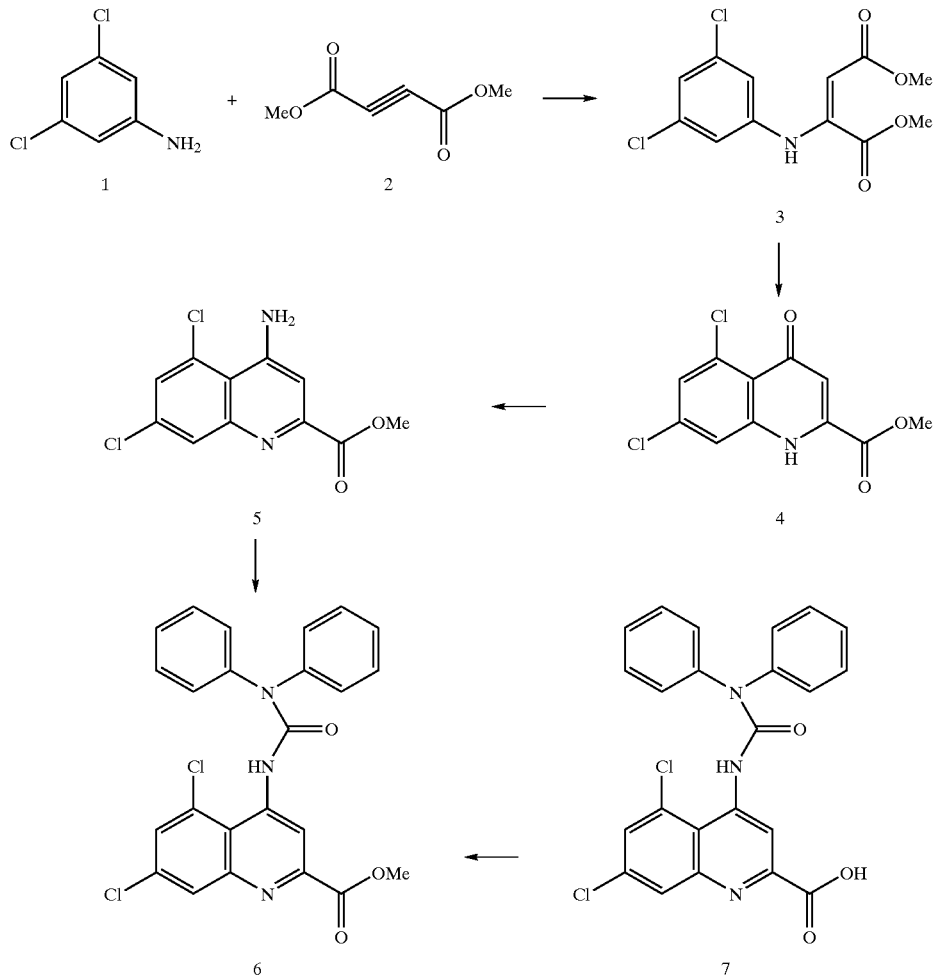

Synthesis Phase I 3,5 Dichloroanaline (1) (3.24 g, 20 mmol) and dimethyl acetylenedicarboxylate (2) (2.46 ml, 2.84 g, 20 mmol) were added under nitrogen with stirring to anhydrous methanol. The mixture was refluxed for 18 hours. The solution was evaporated under reduced pressure to give a bright yellow solid. Recrystallization (twice) from methanol yielded the dimethyl anilinofumarate (3) as a yellow crystalline solid (1.6 g). The absorption peak values (in ppm) found in the $^1$H NMR spectrum of the intermediate dimethyl anilinofumarate compound
were 3.8 (6H, 2×s), 5.6 (1H, s), 6.8 (2H, s), 7.1 (1H, s), 9.6 (1H, broad s). The $^{13}$C NMR spectrum values found were 51.5, 53.0, 97.1, 118.8, 123.9, 135.3, 142.3, 146.1, 164.0, 169.4.

Synthesis Phase II

The dimethyl anilinofumarate was cyclized as follows. Dimethyl anilinofumarate (3) (1 g) was added portionwise, with vigorous stirring to diphenyl ether (20 ml) which was maintained within the range of about 240 to about 260° C. (about 464 to 500° F.) under nitrogen. The mixture was stirred at about 245° C. (about 473° F.) for an hour, then allowed to cool to room temperature (about 21–23° C.). The suspension was diluted with hexanes, at which point the product precipitated. The mixture was filtered, and the filtrate washed thoroughly with hexanes. Recrystallization from ethanol gave the 4(1H)-quinolone-2-carboxylate compound (4) as a creamy white solid.

Synthesis Phase III

The 4(1H)-quinolone-2-carboxylate was aminated as follows. Cholorosulphonyl isocyanate (0.2 mmol, 28 mg, 17 μl) was added to a solution of the quinolone compound (4) (50 mg., 0.19 mmol) in dry acetonitrile (5 ml) at room temperature (about 21–23° C.). The resulting mixture was heated to reflux for about 2 hours (until the evolution of carbon dioxide ceased). A solution of HCl in dry methanol was added, and the reaction mixture cooled to ambient room temperature. Evaporation and crystallization from methanol yielded the salt of the aminoquinoline. This salt compound was dissolved in water, neutralized with a sodium carbonate solution (8%), and extracted twice with ethyl acetate (25 ml each extract). The organic extracts were combined, dried over magnesium sulfate, filtered and evaporated to give the amino quinoline compound (5), which was purified by crystallization from methanol. The absorption peak values (in ppm) found in the $^1$H NMR spectrum for the amino quinoline (5) compound were 4.2 (3H, s), 6.2 (1H, broad s.), 7.4 (1H, s), 7.45 (1H, s), 7.6 (1H, d, J=2.2 Hz), 8.2 (1H, d, J=1.95 Hz).

Synthesis Phase IV

The amino quinoline compound was acylated as follows. Freshly washed sodium hydride (NaH) was added portionwise to a stirred solution of the quinoline compound (5) (20 mg., 0.075 mmol) in dried tetrahydrofuran (THF) (2 ml) under nitrogen. The mixture was stirred at room temperature for about 30 minutes. Diphenyl carbamoyl chloride was then added, and the mixture was allowed to stir for about 24 hours with Thin Layer Chromatography (TLC) monitoring (1:1, ethyl acetate-hexanes). At this point the reaction was seen to be incomplete, as evidenced by a remainder of starting material. A further equivalent amount of the NaH and the carbamoyl chloride was added and the reaction was allowed to stir further for about 18 hours at ambient room temperature at which point no starting material remained. The mixture was evaporated under reduced pressure and flashed with 3:7 ethyl acetate-hexanes to give carbamoyl chloride and other co-products. Elution with 4:6 and then with 1:1 ethyl acetate-hexanes yielded the urea derivative, (N,N-diphenyl)-4-ureido-5,7-dichloro-2-carboxy methyl ester (6) compound (DCUK-OMe), as a white solid, which was recrystallized from diethyl ether (20 mg). The absorption peak values (in ppm) found in the $^1$H NMR spectrum for the DCUK-OMe compound (6) were 4.1 (3H, s), 7.4–7.7 (m, 13H), 8.3 (1H, d, J=2.44 Hz), 9.5 (1H, s), 9.6 (1H, broad s).

Synthesis Phase V

The DCUK-OMe compound was then hydrolyzed as follows. The DCUK-OMe compound (6) (3.5 mg) was dissolved in THF (5 ml) and lithium hydroxide (0.01 mmol, 0.24 mg) in water (100 μl) was added, followed by water (2 ml). The mixture was stirred vigorously at ambient room temperature (about 21–23° C.) with TLC monitoring (1:1 ethyl acetate-hexanes). After about 24 hours the ester (Rf 0.5) had disappeared in favor of another spot on the baseline. The THF was evaporated under reduced pressure and a further 20 ml of water was added to the remnants. Adjustment of the pH of the solution to a pH of 1 gave a white precipitate. The suspension was washed twice with ethyl acetate (20 ml). The combined organic extracts were washed with brine and dried over magnesium sulfate. Filtration and evaporation yielded the final carboxylic acid, (N,N-diphenyl)-4-ureido-5,7-dichloro-2-carboxy-quinoline (DCUKA) compound (7), as a white solid which was recrystallized from diethyl ether. The absorption peak values (in ppm) in the $^1$H NMR spectrum for the DCUKA compound (7) was 7.2–7.4 (H, m), 7.6 (1H, s), 8.0 (1H, s), 8.9 (1H, s), 9.1 (1H, s).

Alternatively, the DCUKA compound can be prepared as illustrated below.

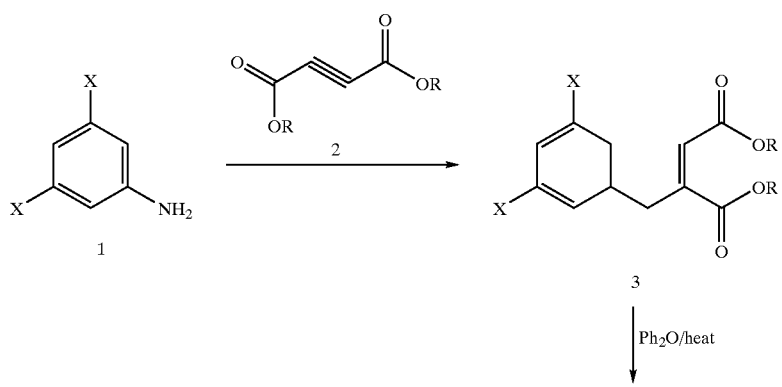

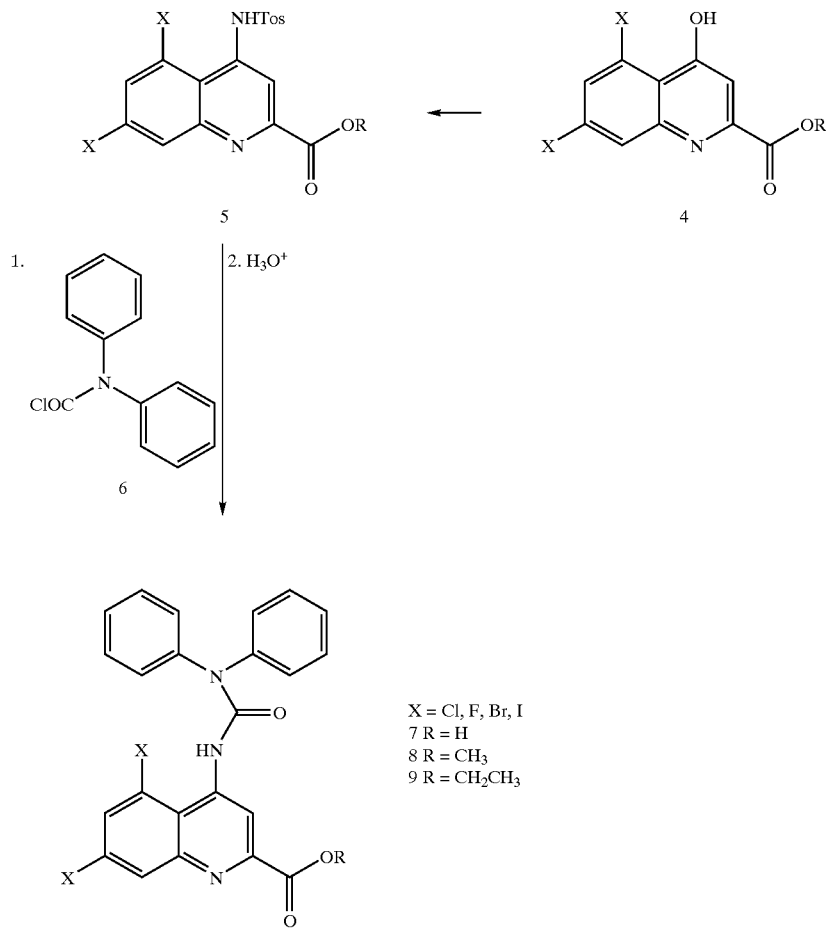

The dichloroquinoline (represented by 4) may be synthesized as described by Heindel, N. D., et al., "CYCLIZATION OF ANILINE-ACETYLENE DICARBOXYLATE ADDUCTS: A MODIFIED CONRAD-LIMPACH METHOD FOR THE SYNTHESIS OF POTENTIAL ANTIMALARIALS," J. Med. Chem. 11 1218–1221 (1968). 3,5-Dichloroaniline, (1) a dihaloaniline, is refluxed with dimethyl acetylenedicarboxylate to produce substituted diester (3) in approximately 80% yield. Upon heating in diphenyl ether, the fumarate ester under goes cyclization to the quinoline carboxylate (4). The ester (4) can be readily aminated to the tosylamine (5) as described by Harrison, B. L., et al., "4-[(CARBOXYMETHYL)OXYL]-AND 4-[(CARBOXYMETHYL)AMINO]-5,7-DICHLORO-QUINOLINE-2-CARBOXYLIC ACID: NEW ANTAGONISTS OF THE STRYCHNINE-INSENSITIVE GLYCINE BINDING SITE ON THE N-METHYL-D-ASPARTATE RECEPTOR COMPLEX," J. Med. Chem. 33 3130–3132 (1990). The tosylamine (5) was acylated with diphenylcarbamoyl chloride (6), followed by hydrolysis, to form the diphenyl urea derivative (7).

The following examples are for illustrative purposes only and are not to be construed as limiting this invention in any manner.

EXAMPLE 1

Effect of DCUK Compounds on the Binding of [$^3$H]5,7-DCKA to Rat Brain Cortical Membranes and [$^3$H]BTX Binding to Rat Brain Cortical Synaptosomes This example compares the effect of DCUK compounds on the binding of ligands defining the strychnine-insensitive glycine binding site on the NMDA receptor, and batrachotoxin binding to a site on voltage-sensitive sodium channels, to effects of the DCUK compounds on binding of ligands defining other binding sites and receptors in rat brain cortical preparations.

Male Sprague-Dawley rats were killed, their brains removed, and their cerebral cortices dissected and binding of [$^3$H]5,7-dichlorokynurenate ([$^3$H]5,7-DCKA) assayed. [$^3$H] 5,7-DCKA binding assays were performed in crude synaptic membranes prepared by a modification of the method of Jones, et al., J. Pharmacol. Methods, 21 161–168 (1989) the relevant disclosures of which are incorporated herein by reference. The pelleted "buffy coat" fraction was obtained by centrifugation and frozen at about −80° C. for at least 18 hours. On the day that the binding assays were performed, the pelleted membranes were resuspended in 50 mM HEPES-KOH buffer (pH 7.8) containing 0.08% TRITON® X-100. After stirring for about 30 min at about 4° C., the membranes were pelleted by recentrifugation and then washed twice by resuspension in buffer and centrifugation.

[$^3$H]5,7-DCKA binding assays were performed employing the well known procedure of Baron, B. M., et al., a description of which can be found in "[$^3$H]5,7-DICHLOROKYNURENIC ACID, A NOVEL RADIOLIGAND LABELS NMDA RECEPTOR-ASSOCIATED GLYCINE BINDING SITES," *Eur. J. Pharmacol.-Mol. Pharmacol. Sec.*, 206 149–154 (1991), the relevant disclosures of which are incorporated herein by reference. Binding assays were performed in 0.5 ml volume using 150–200 μg of tissue, 20 nM [$^3$H]5,7-DCKA and 3–300 μM DCUKA or MeO-DCUKA or 1–100 μM DCUK-OMe (all concentrations are final concentrations in 0.6% dimethyl sulfoxide (DMSO)). Incubations were performed for about 45 min at about 4° C. followed by termination by centrifugation. Bound radioactivity was quantitated by liquid scintillation spectroscopy. Non-specific binding was defined with 1 mM glycine.

The results obtained are plotted in FIG. 1A and are compared in Table 1A below to carbamazepine. From FIG. 1A and Table 1A, it is apparent that the DCUK compounds produced a concentration-dependent decrease in [$^3$H]5,7-DCKA binding suggesting that these compounds have affinity for the strychnine-insensitive glycine site on the NMDA receptor complex.

[$^3$H]Batrachotoxinin ([$^3$H]BTX) binding assays (defining binding to the voltage sensitive sodium channels) were performed in freshly prepared rat cortical crude synaptosomes according to the well-known method of Willow, M., et al. A description of the method can be found in Willow M., et al., "INHIBITION OF BINDING OF [$^3$H]BATRACHOTOXININ A 20-ALPHA-BENZOATE TO SODIUM CHANNELS BY THE ANTICONVULSANT DRUGS DIPHENYLHYDANTOIN AND CARBAMAZEPINE," *Mol. Pharmacol.*, 22 627–635 (1982), the relevant disclosures of which are incorporated herein by reference. The crude P$_2$ synaptosomal pellet was obtained by homogenization and centrifugation through 0.32 M sucrose-5 mM K$_2$HPO$_4$. The pellet was resuspended in sodium-free assay buffer containing (in mM) 50 HEPES, 5.4 KCl, 0.8 MgSO$_4$, 5.5 glucose, 130 choline chloride, (pH 7.6) containing 1 μM tetrodotoxin and 1 μg/ml scorpion venom. [$^3$H]BTX binding was performed in 1 ml using 300–400 μg of tissue, 10 nM [$^3$H]BTX, and the same concentrations of the DCUK compounds as those used in the [$^3$H]5,7-DCKA binding assay. Incubations were performed for about 90 min at ambient room temperature (about 21–23° C.) followed by vacuum filtration over GF/C filters. Bound radioactivity was quantitated by liquid scintillation spectroscopy. Non-specific binding was defined with 0.3 mM veratridine. The results obtained are plotted in FIG. 1B and are compared to carbamazepine below in Table 1A.

Figure 1B:
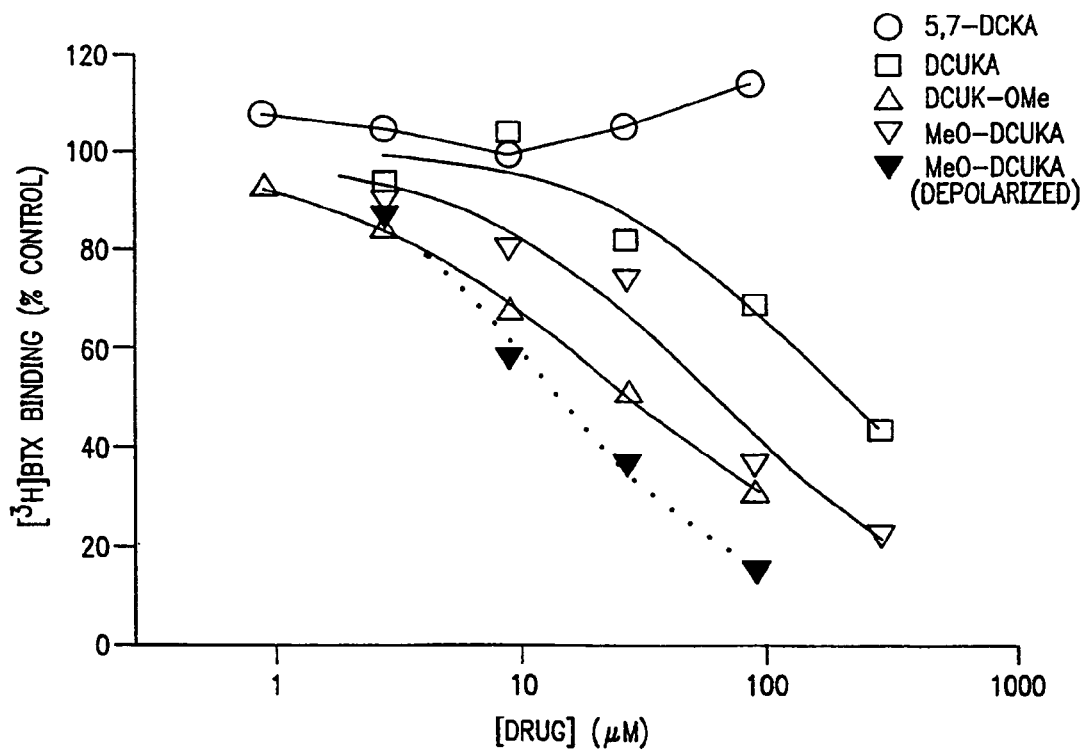

From FIG. 1B and Table 1A below, it is apparent that the DCUK compounds produced a concentration-dependent decrease in [$^3$H]BTX binding, suggesting that, in addition to their affinity at the glycine site of the NMDA receptor, these compounds also have significant affinity for voltage-sensitive sodium channels (VSNaCs). In a separate test, KCl (135 mM) was substituted for choline chloride in the assay buffer in order to depolarize the synaptosomes. As can be seen in FIG. 1B and Table 1A, the affinity of MeO-DCUKA for the [$^3$H]BTX binding site was increased, suggesting that these compounds, like the prototypical sodium channel blocker, carbamazepine, exhibit a voltage-dependent block of VSNaCs.

TABLE 1A

| Compound | IC50 (μM) [$^3$H]5,7-DCKA binding | IC$_{50}$ (μM) [$^3$H]BTX binding |
| --- | --- | --- |
| DCUK—OMe | 5 | 25 |
| MeO—DCUKA | 35 | 64 (30) |
| Carbamazepine | none* | 71 (56) |
| 5,7-DCKA | 0.11 | none |

TABLE 1B

| Ligand | DCUKA IC$_{50}$ (μM) |
| --- | --- |
| [$^3$H]5,7-DCKA | 22 |
| [$^3$H]BTX | 76 |
| [$^3$H]CGP 39653 | >200 |
| [$^3$H]kainate | >200 |
| [$^3$H]flunitrazepam | >200 |
| [$^3$H]rauwolscine | >200 |
| [$^3$H]ifenprodil | >200 |

Notes to Tables 1A and 1B
[$^3$H]5,7 dichlorokynurenate (5,7-DCKA), [$^3$H]CGP 39653, [$^3$H]kainate, [$^3$H]ifenprodil, and [$^3$H]flunitrazepam binding assays were performed in P$_2$-buffy coat membranes prepared from rat forebrain.
[$^3$H]rauwolscine binding was performed in crude P$_1$ membranes.
[$^3$H]Batrachotoxinin (BTX) binding was performed in synaptosomes prepared from rat forebrain. IC$_{50}$ values obtained under non-depolarizing or depolarizing conditions (135 mM KCl; values in parentheses).
none - no displacement at 100 μM.
none* - no displacement at 64 μM carbamazepine. Taken from McCabe, R. T., et at., "Evidence for anticonvulsant and neuroprotectant action of felbamate medicated by strychnine-insensitive glycine receptors,"J. Pharmacol. Exp. Ther., 264 1248–1252, (1993).

Notes to Tables 1A and 1B
[$^3$H]5,7 dichlorokynurenate (5,7-DCKA), [$^3$H]CGP 39653, [$^3$H]kainate, [$^3$H]ifenprodil, and [$^3$H]flunitrazepam binding assays were performed in P$_2$-buffy coat membranes prepared from rat forebrain.

[$^3$H]rauwolscine binding was performed in crude P$^1$ membranes.

[$^3$H]Batrachotoxinin (BTX) binding was performed in synaptosomes prepared from rat forebrain. IC$_{50}$ values obtained under non-depolarizing or depolarizing conditions (135 mM KCl; values in parentheses).

none—no displacement at 100 μM.

none*—no displacement at 64 μM carbamazepine. Taken from McCabe, R. T., et al., "Evidence for anticonvulsant and neuroprotectant action of felbamate medicated by strychnine-insensitive glycine receptors," *J. Pharmacol. Exp. Ther.*, 264 1248–1252, (1993).

In a separate study, 5–200 μM DCUKA was studied for its ability to displace [$^3$H]CGP 39653, [$^3$H]kainate, [$^3$H]ifenprodil, and [$^3$H]flunitrazepam binding. Rat cortical membranes, prepared as described for [$^3$H]5,7-DCKA binding, were used to test whether the DCUK compounds have affinity for the glutamate site of the NMDA receptor, the polyamine binding site on the NMDA receptor, the kainate binding site on non-NMDA glutamate receptors, and the benzodiazepine binding site on the GABA$_A$ receptor, respectively.

[$^3$H]CGP 39653 binding assays were performed according to Sills, M., et al., a description of which can be found in *Eur. J. Pharmacol.*, 192 19–24 (1991) the relevant disclosures of which are incorporated by reference, employing a 1.0 ml volume using 150–200 μg tissue, 2 nM [$^3$H]CGP 39653, in 10 mM HEPES-KOH buffer (pH 7.6 at 4° C.).

Non-specific binding was defined with 0.1 mM L-glutamate. Incubations were for 60 min at 4° C., followed by filtration over GF/B filters.

[$^3$H]Kainate binding assays were performed according to Braitman, D. J., et al., a description of which can be found in "INHIBITION OF [$^3$H]KAINIC ACID RECEPTOR BINDING BY DIVALENT CATIONS CORRELATES WITH ION AFFINITY FOR THE CALCIUM CHANNEL," Neuropharmacology, 26 1247–1251 (1987) the relevant disclosures of which are incorporated by reference, employing a 1.0 ml volume using 150–200 µg tissue, 1 nM [$^3$H]kainate, in 50 mM HEPES-KOH buffer (pH 7.1 at 4° C.). Non-specific binding was defined with 0.5 mM kainate. Incubations were for 60 min at 4° C., followed by centrifugation termination.

[$^3$H]Flunitrazepam binding assays were performed according to Tehrani, M. H., et al., a description of which can be found in "AGE-RELATED LEVELS OF GABA/BENZODIAZEPINE BINDING SITES IN CEREBRUM OF F-344 RATS: EFFECTS OF EXERCISE," Neurobiol. Aging, 16 199–204 (1995) the relevant disclosures of which are incorporated by reference, employing a 0.5 ml volume using 150–200 µg tissue, 1 nM [$^3$H]flunitrazepam, 1 mM GABA, in 50 mM HEPES-KOH (pH 7.4 at 4° C.). Non-specific binding was defined by 10 µM diazepam. Incubations were for 30 min at 4° C., followed by filtration over GF/C filters.

[$^3$H]Ifenprodil binding assays were performed according to Shoemaker, H., et al., a description of which can be found in "BINDING OF [$^3$H]IFENPRODIL, A NOVEL NMDA ANTAGONIST, TO A POLYAMINE-SENSITIVE SITE IN THE RAT CEREBRAL CORTEX," Eur. J. Pharmacol., 176 249–250 (1990), the relevant disclosures of which are incorporated by reference. The assay employed a 1.0 ml volume using 150–200 mg tissue, 2 nM [$^3$H]ifenprodil, in a 50 mM HEPES-KOH (pH 7.4 at 4° C.). Non-specific binding was defined with 10 µM ifenprodil. Incubations were for 120 min at 4° C., followed by filtration over GF/B filters presoaked in 0.1% polyethyleneimine.

In addition, the ability of DCUKA to displace [$^3$H]rauwolscine binding was performed according to Broadhurst, et al., a description of which can be found in "A REASSESSMENT OF THE BINDING OF [$^3$H]RAUWOLSCINE TO MEMBRANES FROM THE RAT CORTEX," Neuropharmacology, 25 287–295 (1986) the relevant disclosures of which are incorporated by reference, to test whether DCUK compounds have affinity for the $\alpha_2$-noradrenergic receptors. Rat cortices were homogenized in 20 volumes of ice-cold HEPES-KOH buffer (20 mM, pH 7.4) and twice centrifuged at 50,000 g for 20 min with an intermediate suspension in fresh buffer. The final pellet was stored at −20° C. in 4 volumes of buffer. The binding of [$^3$H]rauwolscine was performed in a 0.5 ml volume using 250–300 µg tissue and 1 nM [$^3$H]rauwolscine in 20 mM HEPES-KOH buffer (pH 7.4 at 23° C.). Non-specific binding was defined by use of 100 µM norepinephrine. Incubations were for 30 min at 23° C., followed by filtration over GF/B filters.

The results are shown in Table 1B. The data confirm that DCUKA, like DCUK-OMe and MeO-DCUKA, has affinity for both the strychnine-insensitive glycine site on the NMDA receptor complex and for the VSNaCs, but the DCUKA shows little affinity for receptors for other neurotransmitters or other ion channels.

EXAMPLE 2

Effect of DCUK Compounds on the Binding of [$^3$H]dizocilpine to Rat Cortical Membranes In a further study, [$^3$H]dizocilpine binding was assayed in rat cortical membranes prepared as described for [$^3$H]5,7-DCKA binding in Example 1. [$^3$H]Dizocilpine (MK-801) binding assays were performed in a volume of 1 ml containing 100–150 µg of tissue, 5 nM [$^3$H]dizocilpine, 10 µM L-glutamate, 30 µM MgSO$_4$, and 100 or 300 µM DCUKA or 30 or 100 µM DCUK-OMe, in 10 mM HEPES-KOH buffer (pH 7.4 at 23° C.). Incubations were for 30 minutes at room temperature. The reaction mixtures were filtered over GF/B filters presoaked in 0.1% polyethyleneimine. Bound radioactivity was quantitated by liquid scintillation spectroscopy. Non-specific binding was defined with 20 µM dizocilpine. Under these conditions, [$^3$H]dizocilpine binding can be used as a measure of the activation of the NMDA receptor ion channel by glycine. See, for example, Wong, E. H. F., et al.," GLYCINE MODULATES [$^3$H]MK-801 BINDING TO THE NMDA RECEPTOR IN RAT BRAIN." Eur. J. Pharmacol., 142 487–488 (1987).

Figure 2:
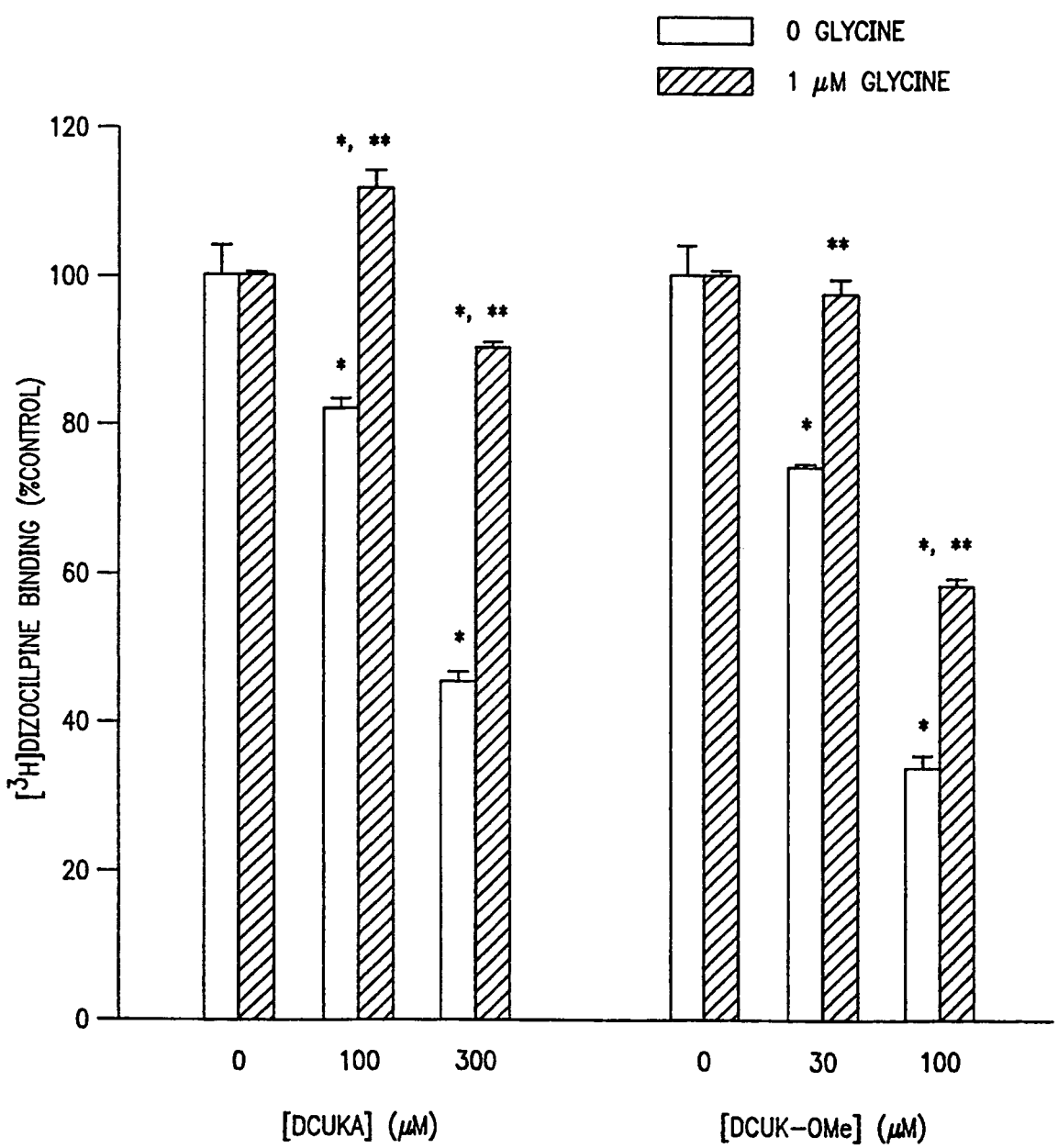
FIG. 2 shows the effects of DCUKA and DCUK-OMe on the binding of [$^3$H]dizocilpine to rat cortical membranes.

The results obtained are plotted in FIG. 2 where open bars indicate no glycine added and hatched bars indicate 1 µM glycine added to the incubation. Data were statistically analyzed by 2-way analysis of variance (ANOVA) followed by Tukey test. In FIG. 2, * denotes P<0.05 compared to the zero concentration of DCUKA or DCUK-OMe within a given glycine condition, while ** denotes P<0.05 compared to the 0 glycine condition at a given concentration of DCUKA or DCUK-OMe. From FIG. 2 it is apparent that, in the absence of exogenous glycine, DCUKA and DCUK-OMe produce a concentration-related decrease in [$^3$H]dizocilpine binding that, upon addition of 1 µM glycine, is significantly attenuated. These data suggest that the DCUK compounds can reduce the activation of NMDA receptor channels by antagonism of the strychnine-insensitive glycine site. Therefore, the DCUK compounds can be classified as antagonists which have actions at the strychnine-insensitive glycine site of the NMDA receptor.

EXAMPLE 3

Effects of DCUKA on NMDA-induced Currents Obtained from Oocytes Expressing Recombinant NMDA Receptors Oocytes were obtained from Xenopus laevis frogs (Nasco or Xenopus I) kept in aquarium tanks at 19–21° C., on a 12 hr light/dark cycle. Mature females were anesthetized by immersion for approximately 30 min in a 0.12% 3-aminobenzoic acid ethyl ester solution, a small incision was made in the abdominal wall and a piece of ovary was removed and placed in Modified Barth's solution (MBS; in mM) containing 88 NaCl, 1 KCl, 10 HEPES, 0.82 MgSO$_4$, 2.4 NaHCO$_3$, 0.91 CaCl$_2$, 0.33 Ca(NO$_3$)$_2$ (pH 7.5). To facilitate manual dissection of oocytes, a section of ovary was transferred from MBS to a hypertonic buffer containing 108 mM NaCl, 2 mM KCl, 2 mM EDTA, 10 mM HEPES, pH 7.5 and theca and epithelial layers of mature oocytes (stages V and VI) were removed with surgical forceps. The follicular layer was removed by a 10 min immersion in 0.5 mg/ml of collagenase in buffer containing 83 mM NaCl, 2 mM KCl, 1 mM MgCl$_2$ and 5 mM HEPES.

Human NR1a, NR2A and NR2B cDNAs in pCDNA-1Amp were transformed and amplified in XL-1 Blue cells and purified with the MaxPrep Qiagen kit. Oocytes were injected with cDNA into the nucleus in the following concentrations: NR1a/2A cDNAs 0.75 ng/30 nl 1:1 ratio, NR1a/2B cDNAs 3.0 ng/30 nl: 1:1 ratio. Injections were made with micropipettes (10 $\mu$m tip diameter) connected to a Drummond micropipettor attached to a micromanipulator. After injection, oocytes were individually placed in wells of 96-well microtiter plates containing incubation medium (MBS supplemented with 10 mg/l streptomycin, 10,000 U/l penicillin G, 50 mg/l gentamicin, 2 mM sodium pyruvate, 0.5 mM theophylline) that had been sterilized by passage through a 0.2 mm filter. Oocytes were incubated at 19° C. for 2 to 4 days after injection.

Oocytes were placed in a rectangular chamber (approximately 100 ml) and perfused (2 ml/min) with frog Ringer (in mM) containing 115 NaCl, 2.5 KCl, 1.8 $CaCl_2$, 10 HEPES (pH 7.2). Oocytes were impaled with two glass electrodes (0.5–10 M$\Omega$) filled with 3 M KCl and clamped at –70 mV using a Warner Instruments (Hamden, Conn.) oocyte clamp (model OC-725C). A strip-chart recorder (Cole-Palmer Instrument Company) continuously plotted the clamping currents. Agonist solutions with or without DCUKA were applied for 20 sec at 5–10 min intervals. Each oocyte represents a single n. Control responses were always measured before and after addition of the DCUKA. The responses to agonist (NMDA) was averaged to account for run-down or run-up that normally occurs with glutamate receptors. Data are expressed as the % inhibition of the agonist response obtained in the absence of the drug.

Figure 3A:
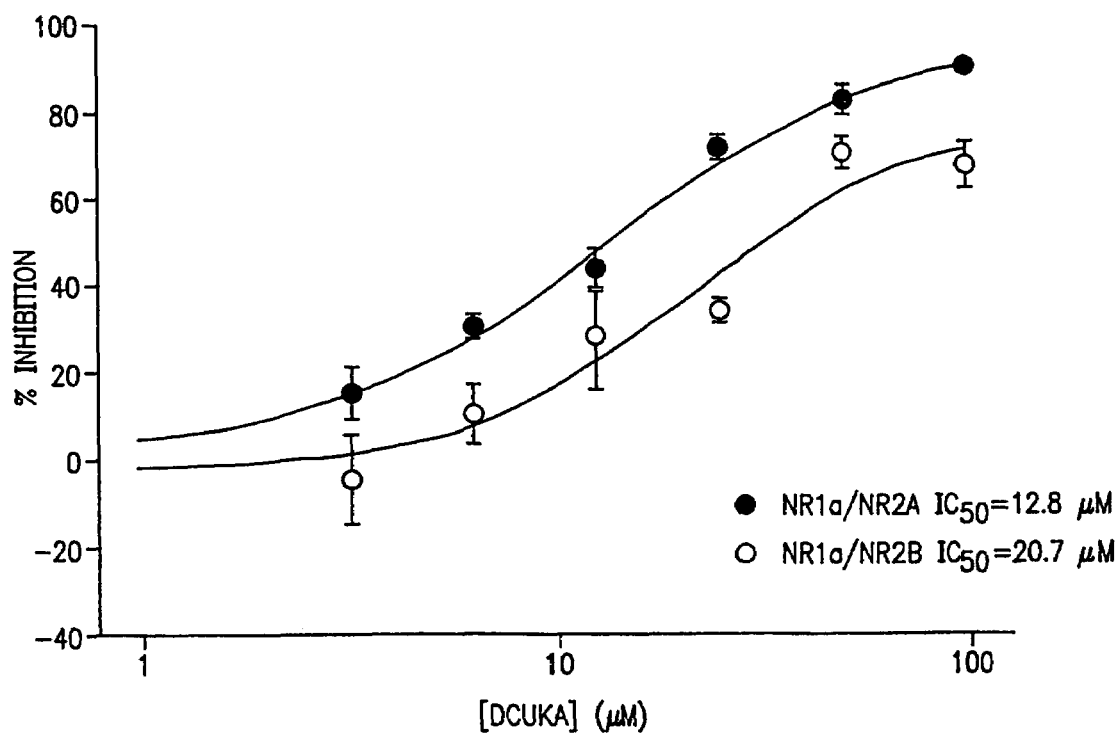
FIG. 3 shows the inhibitory effect of DCUKA on NMDA-induced currents in oocytes expressing recombinant NMDA receptors (3A) and the effects of increasing concentrations of glycine in reversing DCUKA actions (3B-1).

FIG. 3A shows that DCUKA produced a concentration-dependent inhibition of currents generated by application of 100 $\mu$M NMDA in the presence of 1 $\mu$M glycine to oocytes expressing NR1a/NR2A recombinant receptors ($IC_{50}$=12.8 $\mu$M) or 100 $\mu$M NMDA in the presence of 0.3 $\mu$M glycine to oocytes expressing NR1a/NR2B recombinant receptors ($IC_{50}$=20.7 $\mu$M). The concentration of glycine chosen was that which, in combination with NMDA, produced a half-maximal response in oocytes expressing the given NR1a/NR2 heteromer. These affinity estimates are in good agreement with those determined in the [$^3$H]5,7-DCKA binding assay and demonstrate in a physiological system the antagonism of NMDA receptor function. The lower potency of DCUKA for NR1a/NR2B receptors is likely a result of the higher affinity of this subunit combination for glycine compared to NR1a/NR2A receptors (Williams, K., et al., "SENSITIVITY OF THE N-METHYL-D-ASPARTATE RECEPTOR TO POLYAMINES IS CONTROLLED BY NR2 SUBUNITS," *Mol. Pharmacol.*, 45 803–809, 1994).

Figures 1, 3B:
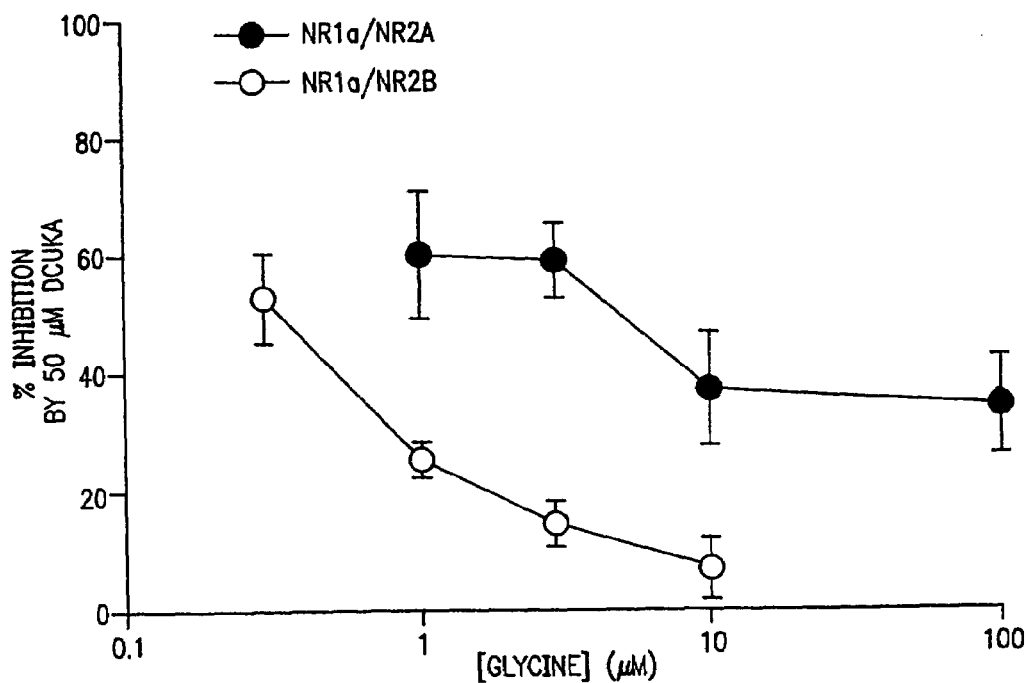
Figures 2, 3B:
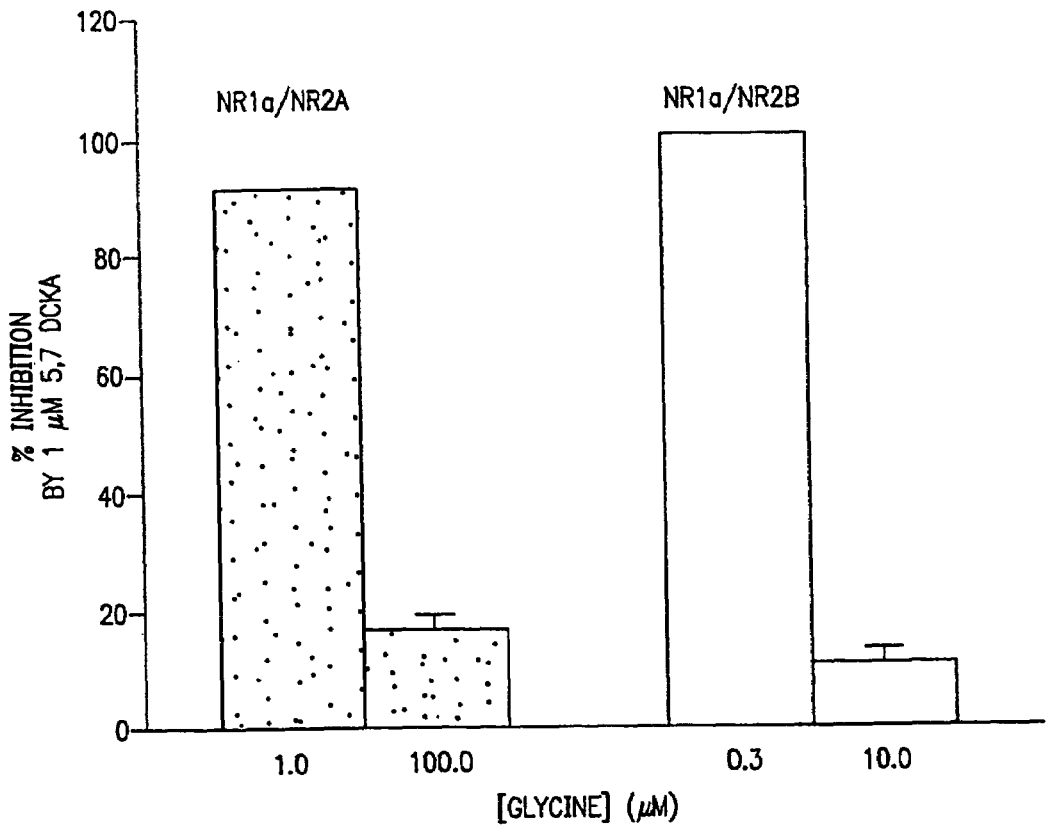

FIG. 3B-1 demonstrates that when the inhibition of NMDA (100 $\mu$M)-induced currents by 50 $\mu$M DCUKA was tested in the presence of increasing concentrations of added glycine, the amount of inhibition by DCUKA of NR1a/NR2B receptors was completely reversed at 10 $\mu$M glycine. This demonstration provided further support that the DCUK compounds antagonize the NMDA receptor by competitively binding to the glycine site of the NMDA receptor composed of NR1a/NR2B subunits. However, the inhibition of NMDA-induced currents in oocytes expressing NR1a/NR2A receptors by 50 $\mu$M DCUKA could not be overcome by glycine, even at a 100 $\mu$M concentration. These data are consistent with a non-competitive antagonism by the DCUKA of NMDA receptor function when the receptors are comprised of NR1a/NR2A subunits. These actions of DCUKA on NMDA receptors comprised of NR1a/NR2A subunits contrast with those of the classic NMDA receptor glycine site antagonist (5,7-DCKA) (FIG. 3B-2), which competitively antagonizes NMDA receptors regardless of subunit composition.

EXAMPLE 4

Effects of DCUKA on Sodium Currents Obtained from CHO Cells Stably Expressing VSNaCs and the Effect of DCUKA on Calcium Currents Obtained from Oocytes Expressing Voltage-sensitive Calcium Channels (VSCCs)

Chinese hamster ovary (CHO) cells stably expressing RSM ($\mu$l) sodium channels were studied using the patch clamp whole cell recording technique. CHO cells were grown to confluence in Dulbecco's Modified Eagle's Medium fortified with 15% FBS, 100 U/ml penicillin and 100 $\mu$g/ml streptomycin in a humidified incubator at 37° C. and 5% $CO_2$, with medium changed every 2–3 days. Transfections with the plasmid pZem$\mu$1–2 were performed using the calcium phosphate coprecipitation method. After 24 hr of incubation with DNA, standard culturing conditions were resumed. After 3 days, stably transfected cells were selected with 400 $\mu$g/ml geneticin. Transfected cells were grown to confluence and then plated on 35 mm culture dishes for 24–96 hr before the experiment.

An 8900 Dagan patch clamp amplifier with a 1 G$\Omega$ 8920 Dagan headstage was used in combination with a Nikon Diaphot inverted microscope. Micromanipulators were used to place the electrode onto the cell. Electrodes were pulled to a resistance of 1–2 Mn. The external solution was (in mM) 132 NaCl, 4 KCl, 0.4 $CaCl_2$, 0.4 $MgCl_2$, 5 glucose, 20 sucrose and 5 HEPES, while the internal solution was 90 CsF, 60 CsCl, 11 NaCl, and 5 HEPES (pH 7.4). Pulse protocols were generated using a 486 PC computer running pCLAMP 5.0 (Axon Instruments, Foster City, Calif.). The cell was held at –100 mV, stepping to various depolarizing potentials (ranging from –80 to 100 mV in increments) for 9 ms, and then returning to the holding potential. Consecutive steps were carried out every 1.5 sec and the data were leak subtracted using the P/4 method, stepping negatively from the –100 mV holding potential. Peak currents were determined from these traces. DCUKA dissolved in 0.4% DMSO was added directly to the bath following seal formation and the data are expressed as the % of the initial peak current response obtained before drug addition. The results are the mean±S.D. of three separate preparations.

Figure 4:
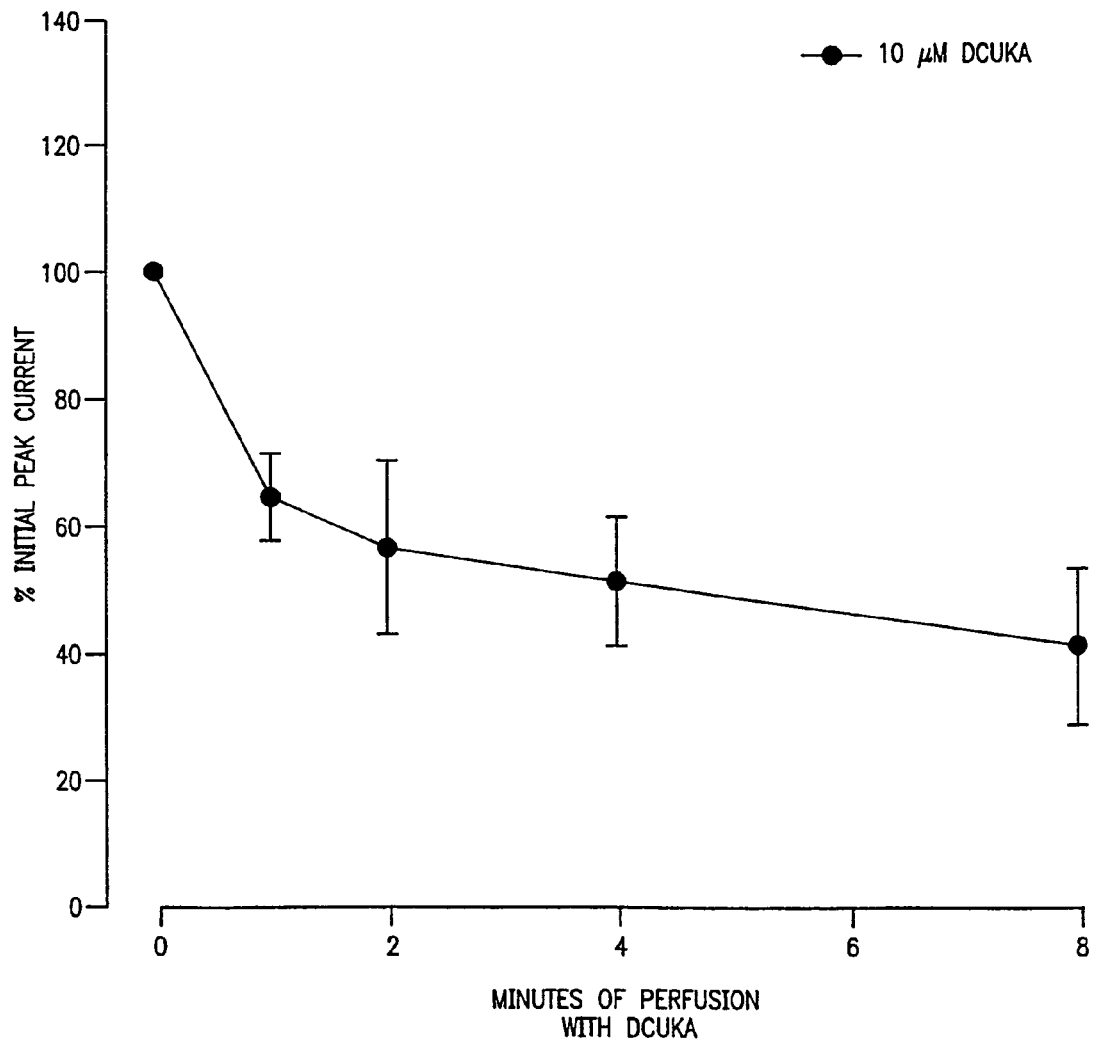
FIG. 4 shows the effect of DCUKA on sodium currents obtained from CHO cells stably expressing VSNaCs.

The DMSO vehicle, although producing an initial drop in current amplitude, produced no lasting effect, and the control current returned to pre-drug or vehicle levels (i.e., 3.3±0.7nA) within one minute of perfusion. The DCUKA-mediated decrement in current through VSNaCs in this preparation and the increasing inhibition of the response with successive depolarizations substantiate the data obtained with measures of [$^3$H]BTX binding that the DCUKA is a use- and voltage-dependent inhibitor of VSNaCs. The data are shown in FIG. 4.

In other studies, Stage V and VI oocytes were prepared from *Xenopus laevis* and maintained using the procedures described in Example 3. Oocytes were injected with cRNA encoding the rabbit cardiac L-type VSCC $\alpha_{ic}$, together with the ancillary subunits $\alpha_2/\beta$ and $\beta_{2b}$, in a 1:1:1 molar ratio. Macroscopic currents were recorded 4–6 days following injection using the two electrode voltage clamp technique. During recording, oocytes were maintained at room temperature in a perfusion chamber and perfused (1 ml/min) continuously with a buffer containing (in mM) 100 LiCl, 10

HEPES, 10 HEDTA, 14 TEA-Cl, 0.015 CaCl$_2$, (effective free calcium concentration ~3 nM), pH 7.4 with TEA-OH. The monovalent ion Li$^+$ was used as the charge carrier rather than Ba$^{2+}$ in these studies because high concentrations of divalent ions promoted precipitation of DCUKA.

DCUKA was made up as a stock solution in DMSO and used in the studies at a concentration of 50 $\mu$M, resulting in a final DMSO percentage of 0.25%. This concentration of DMSO enhanced Li$^+$ currents to a small extent, however, this was controlled for by exchanging between solutions that were identical except for presence/absence of the drug itself. Pipettes were filled with 3 M KCl and had a typical resistance of 1.5 M$\Omega$. Li$^+$ currents were recorded using an OC-725B amplifier (Warner Instruments), filtered at 1 kHz (4-pole Bessel filter, Warner Instruments) and sampled at 2 kHz. Voltage pulses of 250 ms duration were given every 15 sec. The holding potential was −80 mV and the test potential was −20 mV. Under these conditions, DCUKA produced a non-significant (less than 20%) decrement in the current through VSCCs (data not shown) arguing that the inhibition of VSNaC-mediated currents in CHO cells is not a general inhibition of voltage-sensitive ion channel function.

EXAMPLE 5

Effects of (±)HA-966 and 7-Cl Kynurenic Acid on Ethanol Withdrawal-Induced Seizures in C57BL/6 mice Male C57BL/6 mice were housed individually. One group of mice were each given a measured amount of liquid diet (BioServ) containing 6.7% ethanol (v/v) and a second, control group of mice each received the same diet with maltodextrin substituted isocalorically for ethanol, as their sole nutrient source for 7 days. A description of such a test can be found in Grant, K. A., et al., "ETHANOL WITHDRAWAL SEIZURES AND THE NMDA RECEPTOR COMPLEX," *Eur. J. Pharmacol.*, 176 289–296, (1990), the relevant disclosures of which are incorporated herein by reference. Pair-fed mice were given a volume of liquid diet equal to the average volume that the ethanol-fed mice consumed on the previous day. This treatment regimen produces mice that are functionally tolerant to and physically dependent on ethanol. Beginning at 0700 hours on the eighth day of the diet, ethanol-containing diet was replaced with control liquid diet ("withdrawal").

Withdrawal seizure severity was assessed by measuring the incidence of handling-induced and spontaneous seizures, which were rated on a rating scale of 0 to 4, modified from a rating scale described by Grant, K. A., et al. in the above cited article. The rating scale was as follows: 0, little or no reaction; 1, slight jerkiness upon handling; 2, excitability increasing in magnitude to a clonic-tonic seizure; 3, spontaneous or instantaneous clonic-tonic seizure; 4, death while in a seizure. The mice were rated for seizure severity at 2, 4, 6, 7, 8, 9, 10, 11, 12 and 24 hours after ethanol withdrawal. Groups of ethanol-fed mice were injected intraperitoneally at 0700, 1100 and 1400 hours with saline, 3, 10 or 17 mg/kg (±)HA-966 (FIG. 5A) or 10, 17 or 30 mg/kg 7-Cl kynurenic acid (FIG. 5B).

Figure 5A:
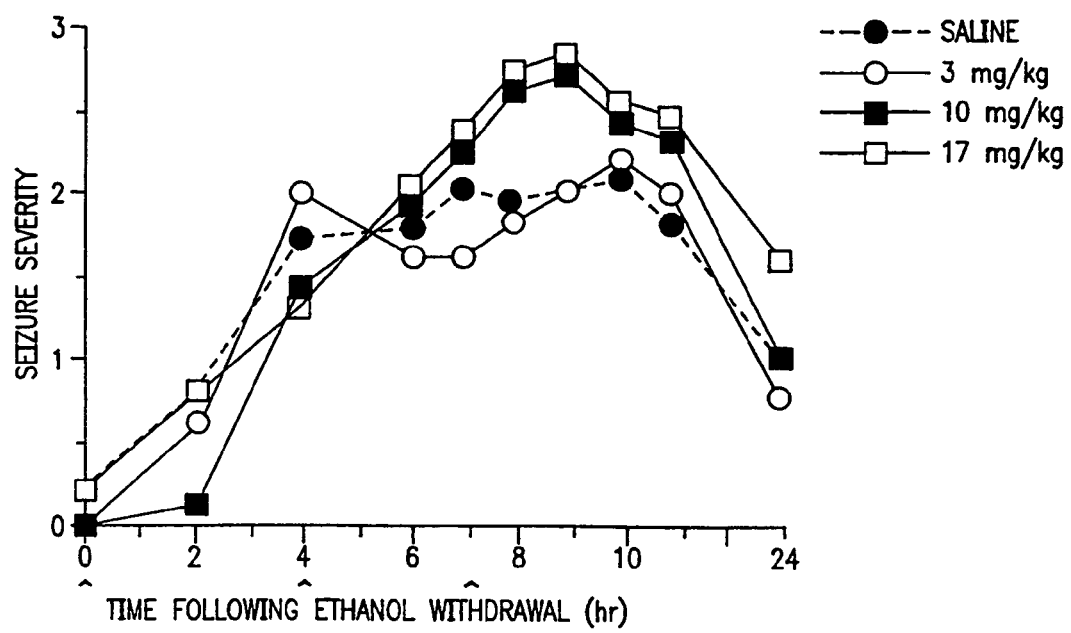
FIG. 5 shows the lack of effects of (±)HA-966 (5A) and 7-Cl kynurenic acid (5B) on ethanol withdrawal-induced seizures in C57BL/6 mice.
Figure 5B:
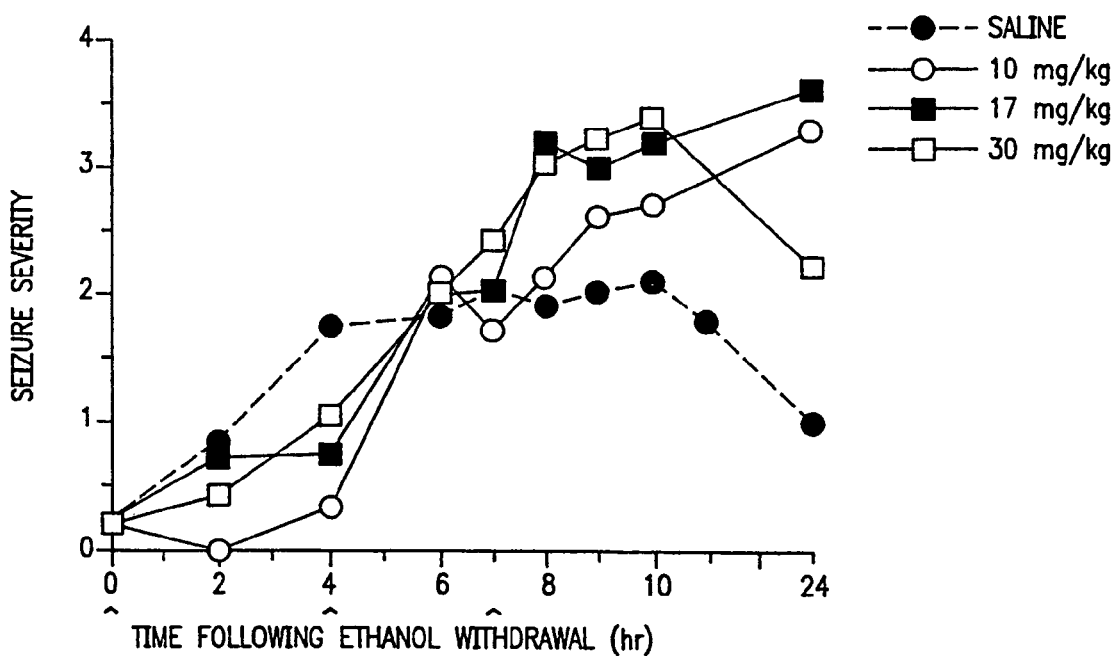

The results presented in FIG. 5A and FIG. 5B, respectively, are the median withdrawal scores of saline-injected (N=6) or drug-injected mice (N=7, each dose). From FIGS. 5A and 5B it can be seen that treatment with (±)HA-966 or 7-Cl kynurenic acid did not significantly reduce seizure severity at any dose or at any time after initiation of withdrawal (P>0.05; Kruskal-Wallis ANOVA). Data obtained in the study of EXAMPLE 14 below additionally illustrates that (±)HA-966 at doses used in the unsuccessful attempts to prevent withdrawal seizures, produce signs of incoordination and ataxia.

Carbamazepine was also administered in doses of 17, 30, or 50 mg/kg at 0700, 1100, and 1400 hours on the day of withdrawal and no significant reduction of severity or the duration of the signs of withdrawal (data not shown) was noted.

EXAMPLE 6

Effects of DCUK-OMe on Ethanol Withdrawal-induced Seizures in C57BL/6 Mice

Male C57BL/6 mice were fed ethanol in a liquid diet and the withdrawal seizure severity was assessed as described in EXAMPLE 5. Groups of ethanol-fed mice received a single injection (i.p.) of either vehicle (4% Tween-80, 0.5% carboxymethylcellulose in 0.9% saline) alone or of 100 mg/kg DCUK-OMe suspended in the vehicle administered at 0900 hours. The results are presented in FIG. 6A as the median withdrawal scores of vehicle-injected (N=14) or DCUK-OMe injected (N=6) mice in which * denotes P<0.05, statistically compared to vehicle-injected mice, in the Mann-Whitney U test. FIG. 6B presents the same data as the total withdrawal score, defined as the area enclosed by the curve connecting median withdrawal scores plotted against time as in FIG. 6A. The mean total withdrawal scores±SEM for the vehicle-injected group and DCUK-OMe-injected groups are plotted in which * denotes P<0.05, statistically compared to vehicle-injected mice, by the Student t-test.

These data suggest that, unlike agents which are solely antagonists of the glycine site of the NMDA receptor ((±)HA-966 and 7-Cl kynurenic acid), or agents that are primarily antagonists of VSNaCs with no affinity for the glycine site of the NMDA receptor, e.g., carbamazepine (see, for example, McCabe, R. T., et al., cited in the notes to Table 1A) and the data in Table 1A, DCUK-OMe, a combined glycine site antagonist and VSNaC blocker, reduces ethanol withdrawal severity.

EXAMPLE 7

Anxiolytic Effects of DCUK-OMe Measured in Swiss-Webster Mice

The anxiolytic effect of the DCUK-OMe was studied in naive Swiss-Webster mice using an elevated plus-maze apparatus. The plus-shaped maze consists of two arms which are open to the environment (about 30×5 cm) and two arms with side and end walls (about 30×5×15 cm). The arms are connected to a central area (about 5×5 cm) and the plus-maze is elevated from the floor to a height of about 50 cm.

All tests were conducted in a sound-attenuated room under low intensity light (25 Watt). Mice were allowed a 30-minute habituation to the darkened testing room after which the mice were placed individually in the central area of the plus-maze facing one of the open arms, and were then allowed to move freely among the open and closed arms. A trained observer blind to the treatment conditions scored the number of entries into open arms, the number of entries into closed arms, the number of entries into the central area, the number of rears, and the number of grooming episodes over a 5-minute period. Between tests, the maze was wiped clean. The percentage open arm entries was calculated for each animal and used as a measure of the anxiolytic/anxiogenic effects of drug treatment. In addition, the total number of entries made into either open or closed arms was recorded as a measure of drug effects on locomotor activity.

Figure 7:
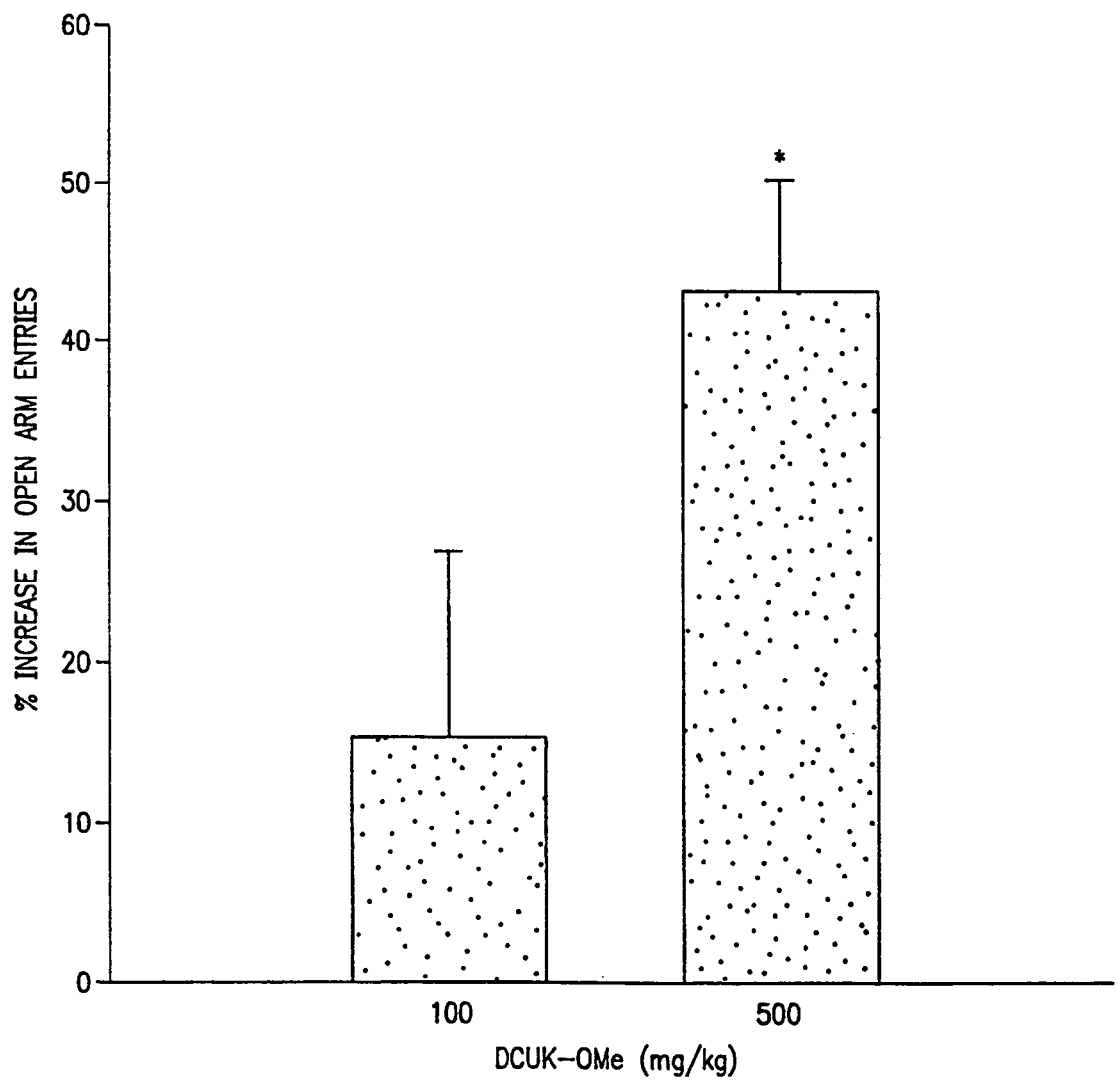
FIG. 7 shows the anxiolytic effects of DCUK-OMe in mice, as measured by use of the elevated plus-maze apparatus.

Mice were injected with either vehicle (5% Tween-80, 20% Intralipid) or 100 mg/kg or 500 mg/kg DCUK-OMe suspended in the vehicle about 90 minutes before testing in the plus-maze apparatus. Data were expressed as the percent increase in open arm entries of the drug treated animals compared to vehicle-injected mice. The results obtained are plotted in FIG. 7. Data were analyzed using a one-way ANOVA on ranks. In FIG. 7, * denotes P<0.05 compared to the vehicle injected mice.

From this data, it is apparent that DCUK-OMe has anxyolitic activity and supports the use of this compound in treating anxiety resulting during drug withdrawal and other anxiety states. It should also be noted that mice receiving injections of either dose of DCUK-OMe did not show any increase in total arm entries compared to vehicle, demonstrating the lack of unwanted stimulatory effects of the DCUK compounds.

EXAMPLE 8

Effect of DCUK-OMe on Audiogenic Seizures Measured in DBA/2J Mice

Figure 8:
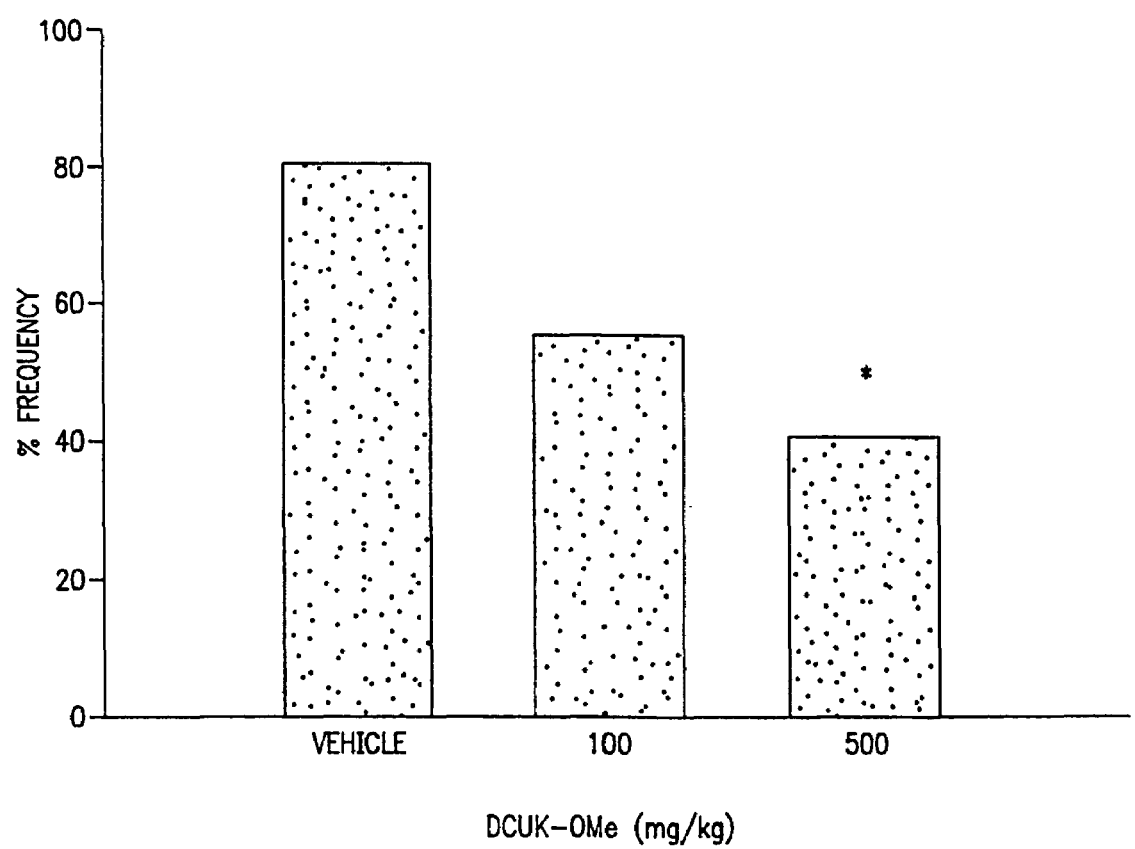
FIG. 8 shows the anticonvulsant effects of DCUK-OMe, as measured by suppression of audiogenic seizures in DBA/2J mice.

Male DBA/2J mice (20–22 days old; 8–12 g) were used to evaluate the effects of DCUK-OMe in an animal model of partial seizures. A description of this test for audiogenic seizures can be found in Engstrom, F. L., et al., "SEIZURE SUSCEPTIBILITY IN DBA AND C57 MICE: THE EFFECTS OF VARIOUS CONVULSANTS," *Epilepsia.*, 29 389–395 (1988), the relevant disclosures of which are incorporated herein by reference. Mice were injected with either vehicle (5% Tween-80, 20% Intralipid) or 100 mg/kg or 500 mg/kg DCUK-OMe suspended in the vehicle about 90 minutes before being placed into a testing chamber having a size of about 6 inches (about 15.2 cm) diameter×about 20 inches (about 50.8 cm) height enclosed in a sound-attenuated box. After a 15–20 second habituation period, a high-intensity auditory stimulus (ringing doorbell, 12–16 kHz, 109 db) was activated for 30 seconds or until tonic hindlimb extension occurred. The seizure response in these mice was characterized by a progression of a wild running behavior, followed by loss of righting and clonus of the forelimbs, followed by tonic hindlimb extension, and finally respiratory arrest. The number of mice showing each response was recorded. FIG. 8 shows the frequency of clonic seizures following administration of the vehicle, 100 mg/kg DCUK-OMe, and 500 mg/kg DCUK-OMe (n=10–20 per group) as described above. Data were analyzed by the Fisher Exact Test. In FIG. 8, * denotes P<0.05 compared to vehicle injected mice. These data indicate that the DCUK compounds provide protection from convulsions arising from conditions other than drug withdrawal.

EXAMPLE 9

Effect of MeO-DCUKA on Kainate (KA)-Induced Seizures

Groups of male C57BL/6 mice were separately given either the vehicle (4% Tween-80, 0.5 carboxymethylcellulose), or 100 mg/kg MeO-DCUKA suspended in the vehicle administered either intraperitoneally (i.p.) or orally (p.o.) about 30 minutes before receiving an injection of kainate (KA) (30 mg/kg, i.p.) and then were observed for the next 4 hours for the presence or absence of KA-induced seizure-related behaviors. KA-induced seizure-induced behavior includes immobility ("staring"), forepaw clonus, clonic-tonic seizures, and death of the animals. The results are shown in Table 2 below.

TABLE 2

| Mice | vehicle/KA (i.p.) | MeO—DCUKA (100 mg/kg, i.p.) | MeO—DCUKA (100 mg/kg, p.o) |
|---|---|---|---|
| # protected/# tested | 4/11 (36%) | 3/6 (50%) | 3/4 (75%) |

From the data in Table 2, it can be concluded that pretreatment with MeO-DCUKA, administered by either intraperitoneal or oral routes substantially protected the animals from KA-induced seizures.

EXAMPLE 10

Effects of DCUK-OMe on Glutamate-induced Excitotoxic Cell Death in Primary Cultures of Rat Cerebellar Granule Cells Primary cultures of cerebellar granule cells were prepared from 6- to 8-day old Sprague-Dawley rats. A description of this procedure can be found in Iorio, K. R., et al., "CHRONIC EXPOSURE OF CEREBELLAR GRANULE CELLS TO ETHANOL RESULTS IN INCREASED N-METHYL-D-ASPARTATE RECEPTOR FUNCTION," *Mol. Pharmacol.*, 41 1142–1148 (1992), the relevant disclosures of which are incorporated herein by reference. The cultures were maintained in plates containing 24 wells of 1 ml each. Culture density was about $1.5 \times 10^6$ cells/ml. Cell viability was assayed after 7–8 days in culture by the production of fluorescein, formed from fluorescein diacetate by esterases present in living cells. A description of this assay can be found in Iorio, K. R., et al., "GLUTAMATE-INDUCED NEUROTOXICITY IS INCREASED IN CEREBELLAR GRANULE CELLS EXPOSED CHRONICALLY TO ETHANOL," *Eur. J. Pharmacol.*, 248 209–212 (1993), the relevant disclosures of which are incorporated herein by reference.

Cells were washed with $Mg^{2+}$-free Locke's buffer, and then exposed to glutamate alone or glutamate in the presence of 10, 30, or 100 $\mu$M DCUK-OMe at 25° C. for 30 minutes. After glutamate exposure, cells were washed twice with buffer and returned to conditioned medium for 24 hours before the fluorescein assay was performed. For each study, the fluorescence value of a control culture (i.e., not exposed to glutamate) was set to 35,000 fluorescence units, and fluorescence values in all other cultures determined using the same spectrofluorometric settings were normalized to that value. One measurement corresponds to the contents of one 1 ml culture well. The data are then expressed as the percent cell death relative to the control cultures.

Figure 9:
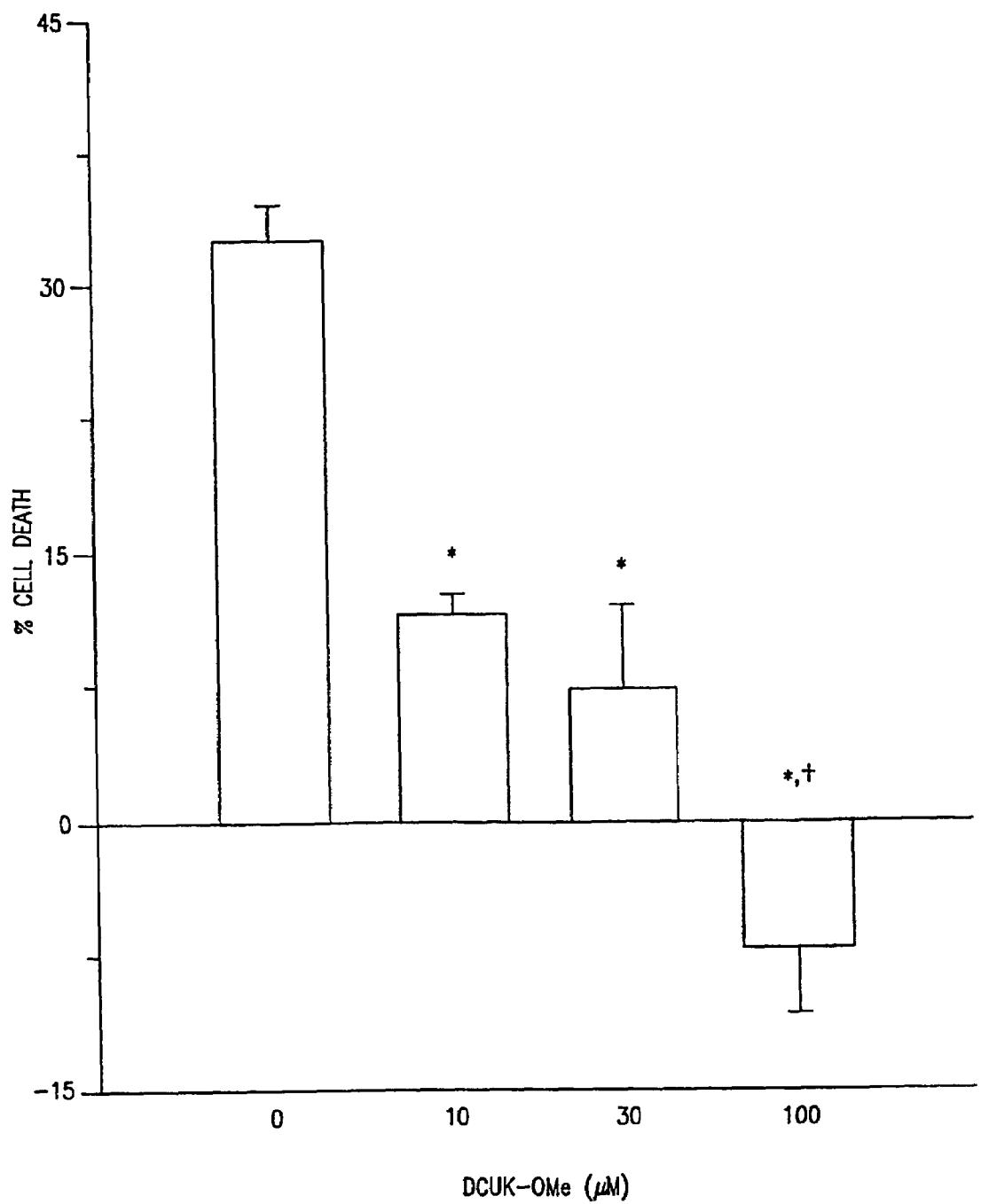
FIG. 9 shows the protective effects of DCUK-OMe on glutamate-induced excitotoxic cell death in primary cultures of rat cerebellar granule cells.

The results obtained are shown in FIG. 9 as the mean±SEM in which * denotes P<0.05, compared to glutamate alone, (ANOVA). From FIG. 9, it can be seen that DCUK-OMe can block glutamate-induced cell death in a concentration-dependent manner, affording complete protection at 100 $\mu$M. These data suggest that the DCUK compounds by virtue of their functional antagonist properties at the NMDA receptor complex through a specific action at the associated strychnine-insensitive glycine site exhibit neuroprotective effects against excitotoxic cell death. In addition, as the influx of Na⁺ secondary to the depolarization induced by glutamate is thought to contribute to cell death. See, for example, Choi, D. W., "EXCITOTOXIC CELL DEATH," *J. Neurobiol.*, 23 1261–1279 (1992), blockade of VSNaCs by the DCUK compounds may afford additional neuroprotective properties.

EXAMPLE 11

Effect of MeO-DCUKA on KA-induced Increase in Heat Shock Protein (HSP72) in the Hippocampus of C57BL/6 Mice In animal models where NMDA receptor-mediated excitotoxic mechanisms have been identified (e.g., KA-induced seizures), an early (24 hours after insult) increase in the 72 kDa heat shock protein (HSP72) levels is detected in brain regions that demonstrate severe neuronal damage and ultimate cell loss. See, for example, Gonzales, M. F. et al., "HEAT SHOCK PROTEINS AS MARKERS OF NEURAL INJURY," *Mol. Brain Res.*, 6 93–100 (1989), the relevant portions of which are incorporated herein by reference.

Groups of male C57BL/6 mice separately received either (1) no injections (Naive), (2) KA injections (30 mg/kg, i.p.), (3) 100 mg/kg MeO-DCUKA administered intraperitoneally, or (4) a pretreatment of 100 mg/kg MeO-DCUKA administered (vehicle as in Example 9) intraperitoneally about 30 minutes before receiving an injection of KA (30 mg/kg, i.p.). All of the mice were killed 24 hours later, their brains removed and the hippocampus dissected. HSP72 protein levels were determined in sodium dodecylsulfate (SDS)-solubilized hippocampal lysates by SDS-PAGE electrophoretic separation and subsequent Western blot analysis using antibodies specific for HSP72/73 proteins. Immunoreactive bands were visualized on film using enhanced chemiluminescence and quantitated by image analysis.

Figure 10:
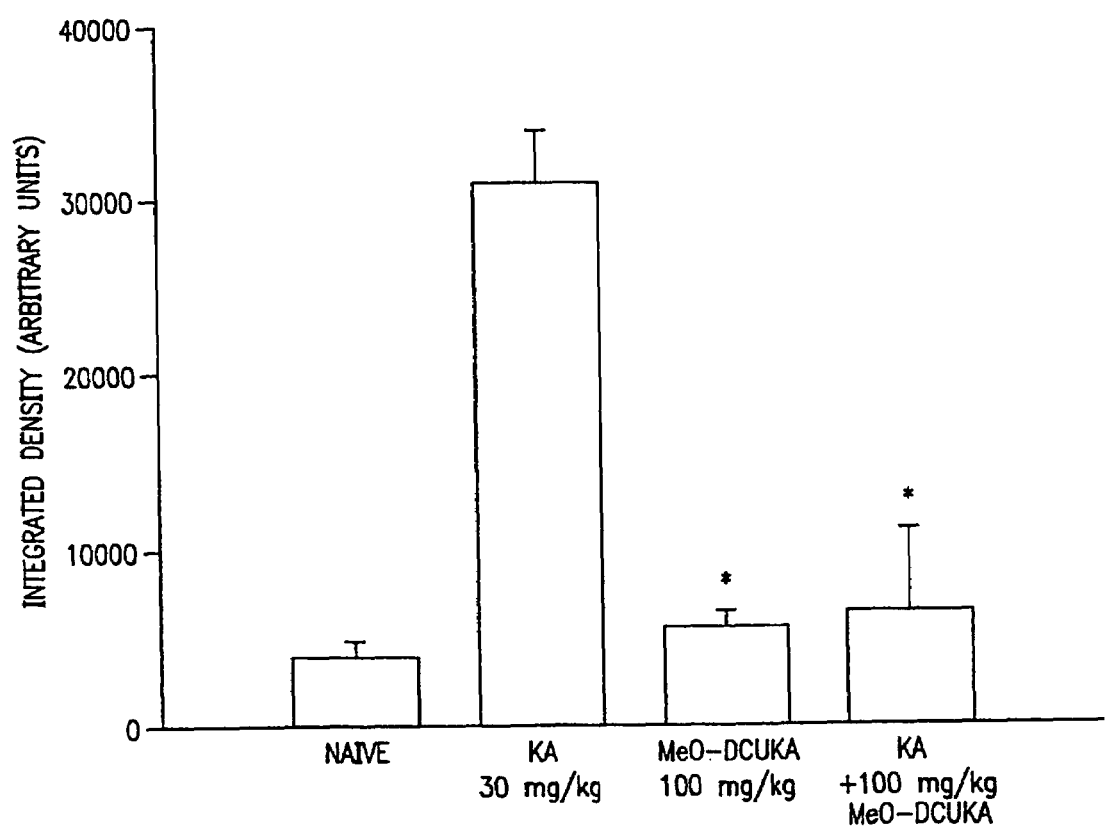
FIG. 10 shows the protective effects of MeO-DCUKA on kainate-induced increases in heat shock protein (HSP72) in the hippocampus of C57BL/6 mice.

The data obtained are graphed in FIG. 10 where * denotes $P<0.01$, statistically compared to all other groups, (ANOVA). From FIG. 10, it can be seen that KA injections produced a significant increase in HSP72 protein levels that was prevented by the 30 min pre-injection pretreatment with 100 mg/kg MeO-DCUKA as described above. These data suggest that MeO-DCUKA affords protection against neuronal injury associated with the excitotoxin, KA.

EXAMPLE 12

Comparison of the Effects of Carbamazepine and Benzodiazepine with DCUK Compounds on the Production of Ataxia/Incoordination Naive Swiss-Webster mice were trained to remain on an accelerating rotarod (diameter 3 cm, 0–30 rpm over 5 min) for six consecutive trials. A description of this test for the acute incoordinating/ataxic effects of sedative/hypnotic drugs such as ethanol can be found in Hoffman, P. L., et al., "EFFECT OF AN IMIDAZOBENZODIAPEZINE, Ro15-4513, ON THE INCOORDINATION OF HYPOTHERMIA PRODUCED BY ETHANOL AND PENTOBARBITAL," *Life Sci.*, 41 611–619 (1987), the relevant disclosures of which are incorporated herein by reference.

The amount of time the mice remained on the rotarod during their last trial was used as their "base-line" score. The mice were then injected (i.p.) with either vehicle (5% Tween-80, 20% Intralipid) (n=10), or 1 mg/kg diazepam (DZP) in vehicle (n=10), or 50 mg/kg carbamazepine (CBZ) (n=5) in vehicle or 100 or 500 mg/kg DCUK-OMe in vehicle. The length of time the mice remained on the rotarod was redetermined at 15, 30, 60, 90, and 120 min after drug injection (i.p.). Results for each mouse at the 30 minute time point were expressed as a ratio (percentage) of their pre-injection base-line time on the rotarod.

Figure 11:
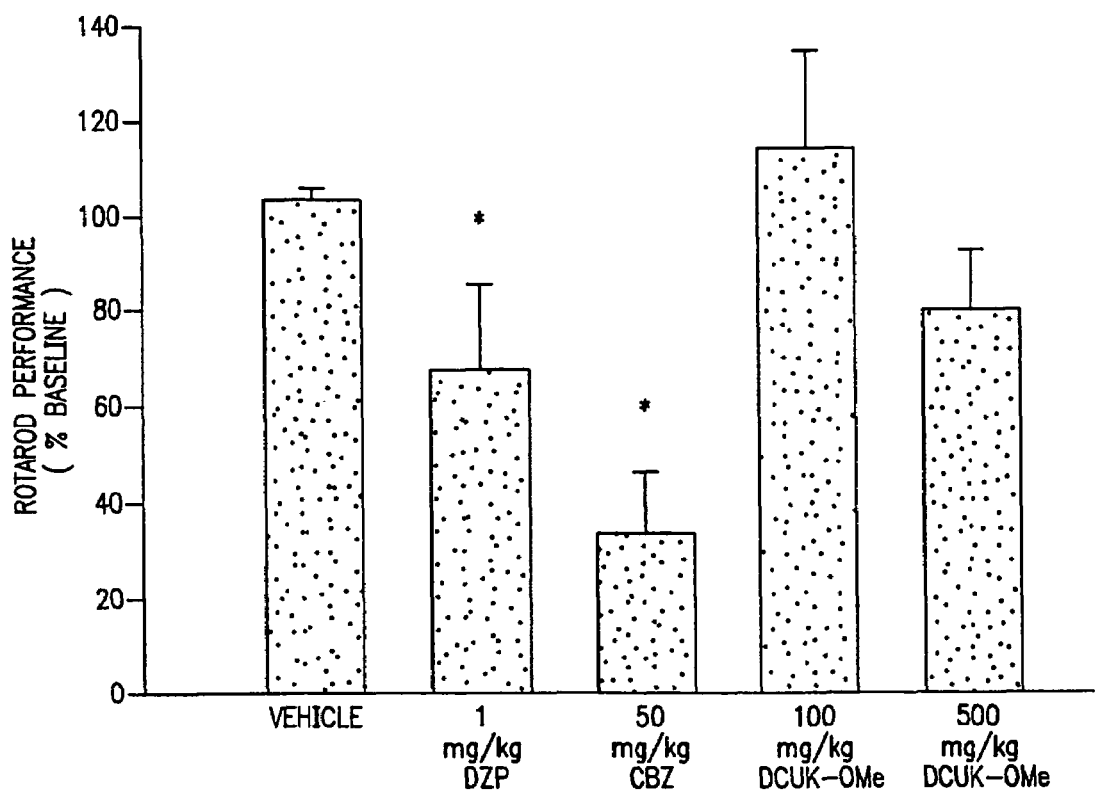
FIG. 11 shows the incoordinating effects of carbamazepine and diazepam on rotarod performance in naive Swiss-Webster mice and lack of incoordinating effects with DCUK-OMe.

The results obtained are plotted in FIG. 11 in which * denotes $P<0.05$ (repeated measures ANOVA following arc-sine transformation of percentage scores) compared to vehicle.

From FIG. 11, it can be seen that mice treated with 50 mg/kg CBZ (a total dose that did not reduce the severity of ethanol withdrawal) were impaired in their ability to remain on the rotarod after the injection.

In contrast, it was noted that naive Swiss-Webster mice administered either 100 mg/kg or 500 mg/kg DCUK-OMe (i.p.) as described above, were able to remain throughout the testing period. These data suggest that DCUK-OMe did not exhibit the same ataxic/incoordinating effects at doses which afford both anticonvulsant and neuroprotective action against the excitotoxin KA and protect against ethanol withdrawal seizures (EXAMPLE 6). On the other hand, it was found that another agent commonly used to treat withdrawal, diazepam (even at a dose of 1 mg/kg), produced significant incoordination of mice on the rotarod. In addition, injection of mice with 50 mg/kg carbamazepine (n=5) also produced significant impairment of ability of mice to remain on the rotarod.

EXAMPLE 13

Figure 12:
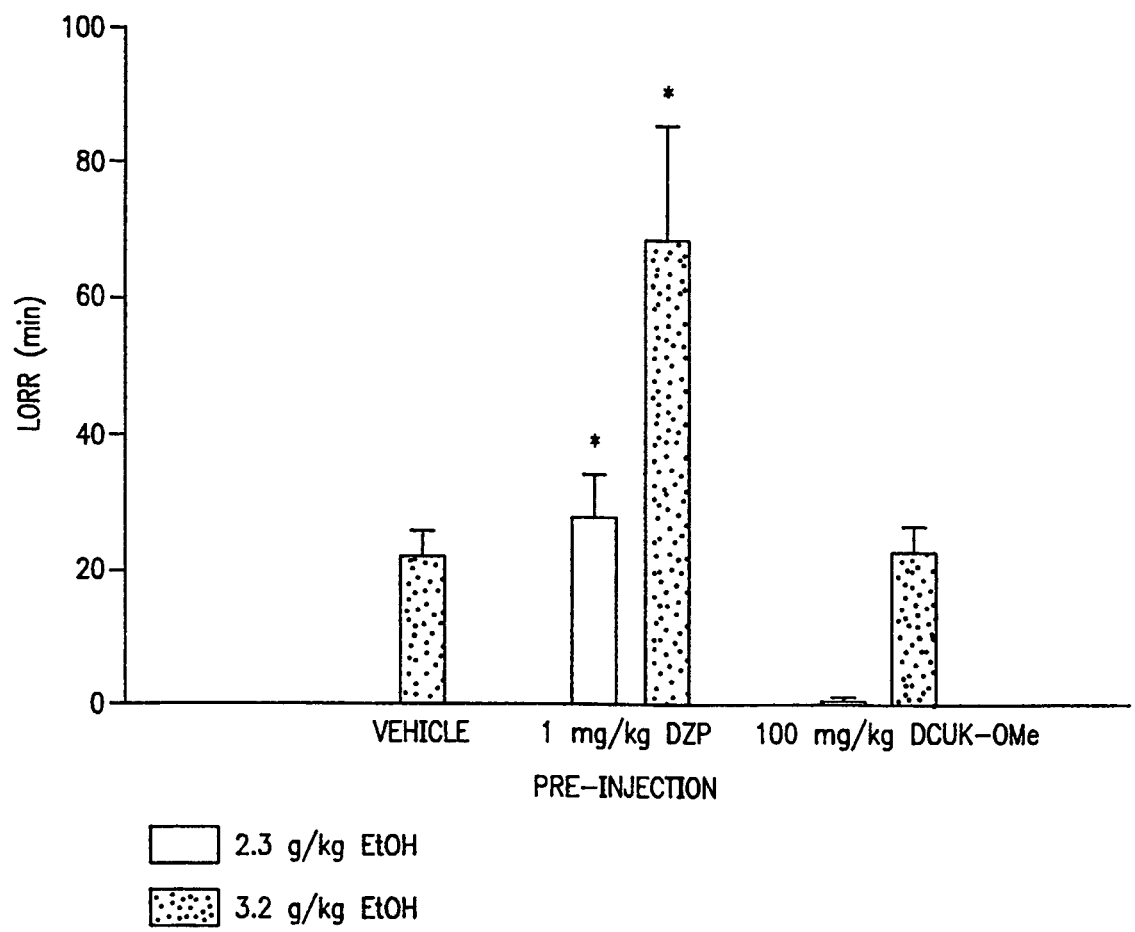
FIG. 12 shows the significant potentiation of the sedative/anesthetic effects of ethanol by diazepam and no significant potentiation of ethanol's actions by DCUK-OMe.

DCUK Compounds do not Potentiate the Sedative/Anesthetic Effects of Ethanol as do Other Agents (i.e., Benzodiazepines) Used for Treatment of Alcohol Withdrawal Swiss-Webster mice were pretreated (i.p.) with 100 mg/kg DCUK-OMe or 1 mg/kg diazepam (DZP) (in 5% Tween-80, 20% Intralipid) 30 minutes before receiving an i.p. administration of ethanol (either 2.3 or 3.2 g/kg, 20% v/v in saline.). The duration of the ethanol-induced loss of righting reflex (defined as the inability of the mouse to right itself when placed on its back in a trough) was measured. The 2.3 g/kg dose of ethanol given alone did not produce a loss of righting reflex while the 3.2 g/kg produced a 20-minute loss of righting reflex. The data shown in FIG. 12 demonstrate a significant (*$P<0.05$) enhancement of the duration of loss by righting reflex (LORR) by DZP and no significant enhancement by DCUK-OMe. Since withdrawal signs are many times evident in individuals whose blood ethanol levels are dropping but are far from zero, the DCUK compounds would have an advantage over DZP in that the CNS depressant effects of ethanol would not be accentuated by DCUK compounds if the DCUK compounds are used in an alcohol-intoxicated individual.

EXAMPLE 14

The Effects of the Glycine Site Antagonist (±)HA-966 on the Production of Ataxia/Incoordination Naive C57BL/6 mice were trained to remain on an accelerating rotarod (diameter 3 cm, 0–30 rpm over 5 min) for six consecutive trials. A description of this test for the acute incoordinating/ataxic effects of sedative/hypnotic drugs such as ethanol can be found in Hoffman, P. L., et al.,

*Life Sciences,* 41 611–619 (1987), the relevant disclosures of which are incorporated herein by reference.

The amount of time the mice remained on the rotarod during their last trial was used as their "base-line" score. The mice were then treated with saline (n=10) or 50 mg/kg (±)HA-966 (n=5). The length of time the mice remained on the rotarod was redetermined at 15, 30, 60, 90, and 120 min after drug injection (i.p.). Results for each mouse at each time point were expressed as a ratio (percentage) of their pre-injection base-line time.

Figure 13:
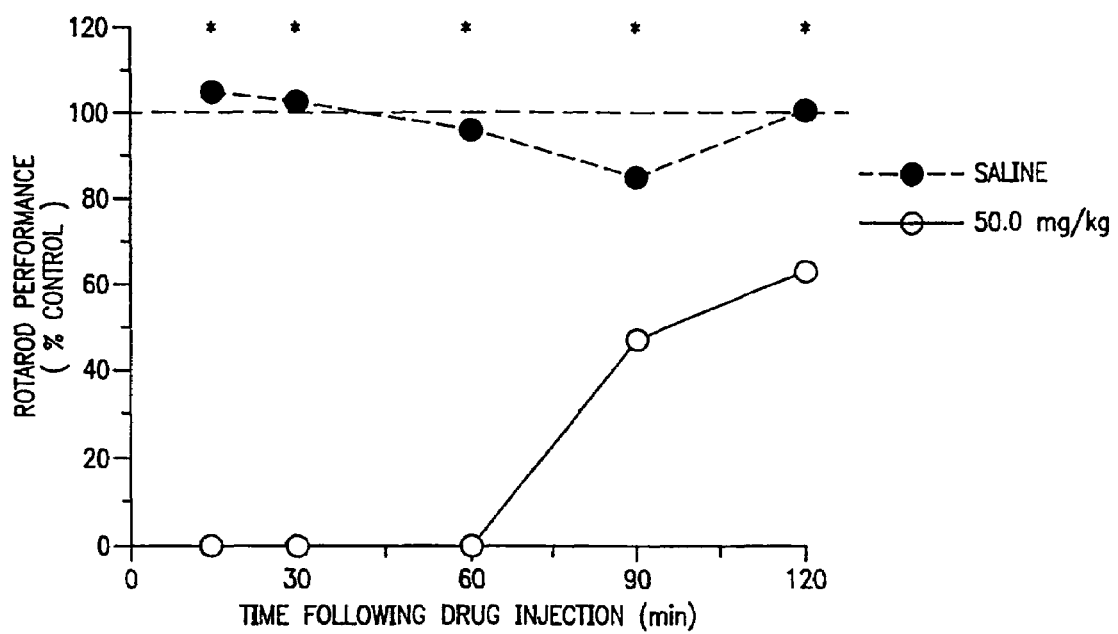
FIG. 13 shows the effects of (±)HA-966 on rotarod performance in naive C57BL/6 mice.

The results obtained are plotted in FIG. 13 in which * denotes P<0.05 compared to (±)HA-966 treated mice (repeated measures ANOVA following arcsine transformation of percentage scores).

From FIG. 13, it can be seen that mice treated with 50 mg/kg (±)HA-966 (a total dose that did not reduce the severity of ethanol withdrawal) were impaired in their ability to remain on the rotarod at all time points tested after the injection. These data indicate that this glycine site antagonist has significant ataxic/incoordinating effects at doses that do not afford protection against ethanol withdrawal seizures.

We claim:

1. A compound having the formula (I):

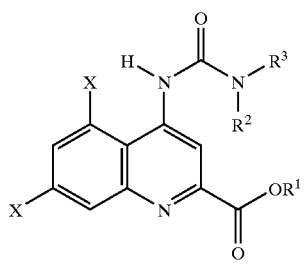

(I)

a tautomer thereof, a pharmacologically acceptable ester, amide, salt, ether, or an acid addition salt thereof;
wherein $R^1$ represents hydrogen or an alkyl group of 1 to 3 carbon atoms;
$R^2$ and $R^3$ each independently represent phenyl which may be unsubstituted or alkoxy substituted one or more times with alkoxy containing 1 to 3 carbon atoms, wherein each of the $R^2$ and $R^3$ substituents can be the same or different; and
X represents halogen and each of the 5, 7, substituents can be the same or different.

2. The compound of claim 1 wherein the compound is selected from the group consisting of (N,N-diphenyl)-4-ureido-5,7-dichloro 2-carboxy-quinoline, (N,N-diphenyl)-4-ureido-5,7-dichloro-2-carboxy-quinoline methyl ester, and N-phenyl, N-[2-methoxy]phenyl)-4-ureido-5,7-dichloro-2-carboxy-quinoline.

3. A compound of claim 1 wherein each of the X substituents is chloro, $R^1$ is hydrogen, and $R^2$ and $R^3$ each is a phenyl group.

4. A compound of claim 1 wherein each of the X substituents is chloro, $R^1$ is an alkyl group having 1 to 3 carbon atoms, and $R^2$ and $R^3$ each is a phenyl group.

5. A compound of claim 1 wherein each of the X substituents is chloro, $R^1$ is hydrogen, one of $R^2$ and $R^3$ is an unsubstituted phenyl group and the other is phenyl having an alkoxy substituent having 1 to 3 carbon atoms.

6. A method of preparing a compound of claim 1 comprising the steps of:
   a) reacting 3,5-dichloroaniline and dimethyl acetylenedicarboxylate to form dimethylanilinofumarate;
   b) cyclizing the dimethylanilinofumarate with diphenyl ether to form 4(1H)-quinolone-2-carboxylate;
   c) aminating the 4(1H)-quinolone-2-carboxylate with chlorosulphonyl isocyanate in acetonitrile to form a 4-aminated derivative thereof; and
   d) acylating the 4-aminated derivative with diphenyl carbamoyl chloride to form (N,N-diphenyl)-4-ureido-5,7-dichloro-2-carboxy-quinoline methyl ester.

7. The method of claim 6 further including the step of:
   e) hydrolyzing the (N,N-diphenyl)-4-ureido-5,7-dichloro-2-carboxy-quinoline methyl ester to (N,N-diphenyl)-4-ureido-5,7-dichloro-2-carboxy-quinoline.

8. The product of the method of claim 6.

9. The product of the method of claim 7.

10. A method for treating a patient to prevent or ameliorate neuroexcitability disorders selected from the group consisting of anxiety and seizure comprising administering to a patient in need of such treatment an effective amount of a compound having the formula (I):

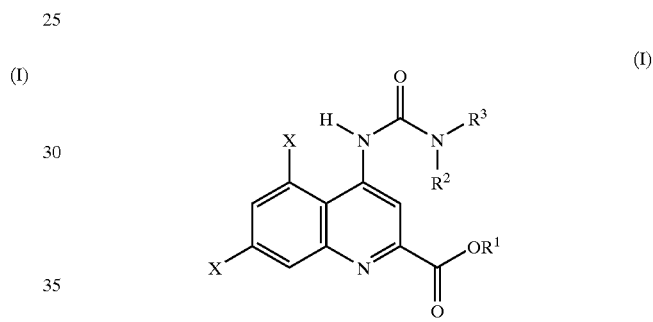

(I)

a tautomer thereof, a pharmacologically acceptable ester, amide, salt, ether, or an acid addition salt thereof;
wherein $R^1$ represents hydrogen or an alkyl group of 1 to 3 carbon atoms;
$R^2$ and $R^3$ each independently represent phenyl which may be unsubstituted or alkoxy substituted one or more times with alkoxy containing 1 to 3 carbon atoms, wherein each of the $R^2$ and $R^3$ substituents can be the same or different; and
X represents halogen and each of the 5, 7, substituents can be the same or different and exhibiting affinity for both the strychnine-insensitive glycine binding site on N-methyl-D-aspartate receptor and voltage dependent sodium channels.

11. The method of claim 10 wherein the compound is selected from the group consisting of N,N-diphenyl-substituted-4-ureido-5,7-dichloro-2-carboxy-quinoline, a tautomer thereof, a pharmacologically acceptable ester, amide, salt, ether and addition salt thereof.

12. The method of claim 10 wherein the compound is selected from the group consisting of (N,N-diphenyl)-4-ureido-5,7-dichloro-2-carboxy-quinoline, (N,N-diphenyl)-4-ureido-5,7-dichloro-2-carboxy-quinoline methyl ester, and N-phenyl, N-[2-methoxy]phenyl)-4-ureido-5,7-dichloro-2-carboxy-quinoline.

* * * * *

UNITED STATES PATENT AND TRADEMARK OFFICE
CERTIFICATE OF CORRECTION

PATENT NO.          : 6,962,930 B1
APPLICATION NO.     : 09/171697
DATED               : November 8, 2005
INVENTOR(S)         : Boris Tabakoff et al.

It is certified that error appears in the above-identified patent and that said Letters Patent is hereby corrected as shown below:

Column 5,
The formula appearing at lines 53-64 should be depicted as follows:

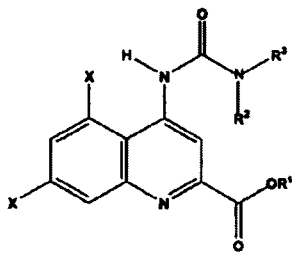

Column 6,
Line 11, "–$NR^a R_b$," should be -- –$NR^a R^b$, --.

Column 8,
The formula appearing at lines 1-13 should be depicted as follows:

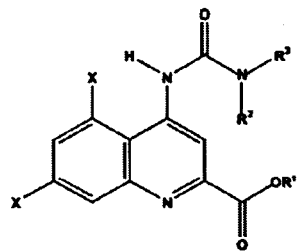

Column 9,
Line 2, after "$R^1$" delete the comma ",".

UNITED STATES PATENT AND TRADEMARK OFFICE
CERTIFICATE OF CORRECTION

PATENT NO. : 6,962,930 B1
APPLICATION NO. : 09/171697
DATED : November 8, 2005
INVENTOR(S) : Boris Tabakoff et al.

It is certified that error appears in the above-identified patent and that said Letters Patent is hereby corrected as shown below:

Columns 14-15,
The formulae bridging columns 14 and 15 should be depicted as follows:

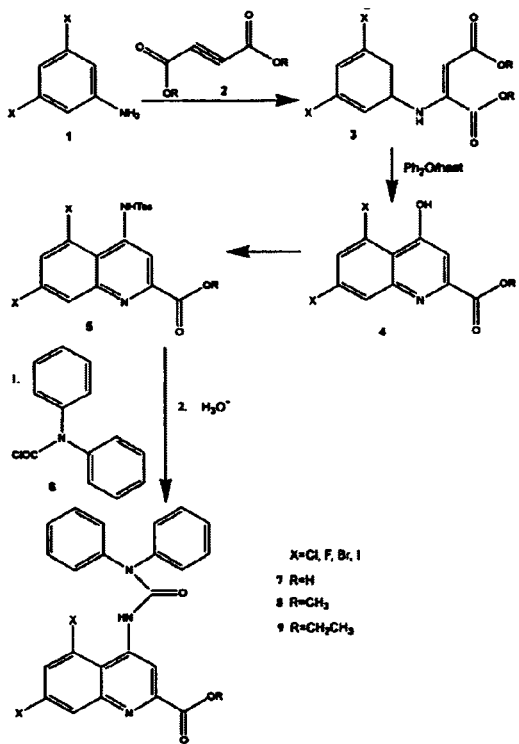

Column 18,
Lines 34-50 should be deleted.

UNITED STATES PATENT AND TRADEMARK OFFICE
CERTIFICATE OF CORRECTION

PATENT NO. : 6,962,930 B1
APPLICATION NO. : 09/171697
DATED : November 8, 2005
INVENTOR(S) : Boris Tabakoff et al.

It is certified that error appears in the above-identified patent and that said Letters Patent is hereby corrected as shown below:

Column 25,
Line 39, "diameterxabout" should be -- diameter x about --.

Signed and Sealed this

Twenty-fourth Day of October, 2006

JON W. DUDAS
*Director of the United States Patent and Trademark Office*